United States Patent
Ausar et al.

(10) Patent No.: US 12,320,753 B2
(45) Date of Patent: Jun. 3, 2025

(54) METHODS FOR DETERMINING ADJUVANTED PROTEIN CONCENTRATION AND PERCENT ADSORPTION USING INTRINSIC FLUORESCENCE

(71) Applicant: Sanofi Pasteur Limited, Toronto (CA)

(72) Inventors: Salvador Fernando Ausar, Markham (CA); Cristopher Roque, Mono (CA); Kirsten April Strahlendorf, North York (CA); Nausheen Rahman, North York (CA)

(73) Assignee: SANOFI PASTEUR LIMITED, Toronto (CA)

( * ) Notice: Subject to any disclaimer, the term of this patent is extended or adjusted under 35 U.S.C. 154(b) by 902 days.

(21) Appl. No.: 16/982,244

(22) PCT Filed: Mar. 19, 2019

(86) PCT No.: PCT/IB2019/052232
§ 371 (c)(1),
(2) Date: Sep. 18, 2020

(87) PCT Pub. No.: WO2019/180618
PCT Pub. Date: Sep. 26, 2019

(65) Prior Publication Data
US 2021/0025827 A1    Jan. 28, 2021

Related U.S. Application Data

(60) Provisional application No. 62/645,367, filed on Mar. 20, 2018.

(51) Int. Cl.
*G01N 21/64*    (2006.01)
*G01N 33/58*    (2006.01)

(52) U.S. Cl.
CPC ....... *G01N 21/6486* (2013.01); *G01N 33/582* (2013.01)

(58) Field of Classification Search
CPC ............... G01N 33/68; G01N 21/6486; G01N 21/8507; G01N 33/582; G01N 2021/8416; G16B 40/10; G16C 20/30
See application file for complete search history.

(56) References Cited

U.S. PATENT DOCUMENTS

2004/0054146 A1* 3/2004 Hellman ............ C07K 16/4291
424/130.1
2004/0116370 A1* 6/2004 Tucker ................... A61K 39/21
514/150

(Continued)

FOREIGN PATENT DOCUMENTS

JP    2007-171213    7/2007
JP    2016-220573    12/2016

(Continued)

OTHER PUBLICATIONS

Chinese Office Action issued Dec. 5, 2023 in corresponding Chinese Patent Application No. 201980032423.2, with English translation.

(Continued)

*Primary Examiner* — Shogo Sasaki
(74) *Attorney, Agent, or Firm* — Wenderoth, Lind & Ponack, L.L.P.

(57) ABSTRACT

Methods and systems for determining the concentration of compounds, such as proteins, in compositions comprising adjuvanted complexes of the compounds are provided. The methods and systems generally comprise (i) measuring the intrinsic fluorescence of a composition comprising adjuvanted complexes of the compound and (ii) comparing the measured fluorescence intensity value to a calibration curve prepared using known concentrations of the compound. Also (Continued)

provided are methods and systems for determining percent adsorption of a selected compound to an adjuvant.

17 Claims, 8 Drawing Sheets

(56) References Cited

U.S. PATENT DOCUMENTS

| | | | |
|---|---|---|---|
| 2004/0214768 A1* | 10/2004 | Holmdahl | A61P 1/04 514/3.3 |
| 2008/0118524 A1* | 5/2008 | Persson | C07K 16/4291 530/387.3 |
| 2010/0253934 A1 | 10/2010 | D'Ascenzi et al. | |
| 2013/0330840 A1 | 12/2013 | Skibinski et al. | |
| 2014/0112954 A1 | 4/2014 | Li et al. | |
| 2021/0149361 A1* | 5/2021 | Jungbauer | G05B 23/0254 |

FOREIGN PATENT DOCUMENTS

| | | |
|---|---|---|
| WO | 2012/052394 | 4/2012 |
| WO | 2012/082914 | 6/2012 |
| WO | 2017/174580 | 10/2017 |

OTHER PUBLICATIONS

Extended European Search Report issued Nov. 12, 2021 in related European Application No. 19771535.2.

International Search Report and Written Opinion of International Searching Authority issued May 22, 2019 in International (PCT) Application No. PCT/IB2019/052232.

Nouchikian et al., "An intrinsic fluorescence method for the determination of protein concentration in vaccines containing aluminum salt adjuvants", Vaccine, vol. 36, 2018, pp. 5738-5746.

Zhu et al., "Use of o-phthalaldehyde assay to determine protein contents of Alhydrogel-based vaccines", Vaccine, vol. 27, 2009, pp. 6054-6059.

Ugozzoli et al., "Flow cytometry: An alternative method for direct quantification of antigens adsorbed to aluminum hydroxide adjuvant", Analytical Biochemistry, vol. 418, 2011, pp. 224-230.

Amari et al., "Concentration Determination of a Recombinant Vaccine Antigen Adsorbed onto an Alum Adjuvant by Chemiluminescent Nitrogen Detection", Pharmaceutical Research, vol. 22, No. 1, Jan. 2005, pp. 33-37.

Wang et al., "Protein Nitrogen Determination by Kjeldahl Digestion and Ion Chromatography", Journal of Pharmaceutical Sciences, vol. 105, 2016, pp. 1851-1857.

* cited by examiner

METHODS FOR DETERMINING ADJUVANTED PROTEIN CONCENTRATION AND PERCENT ADSORPTION USING INTRINSIC FLUORESCENCE

BACKGROUND OF INVENTION

The concentration of antigens in vaccine formulations is a critical parameter that needs to be controlled to ensure consistency in the manufacturing process and product quality. Monitoring the concentration of antigens during production of such formulations is also important for several reasons, such as controlling formulation accuracy, estimating process-related losses, monitoring product homogeneity, and ensuring appropriate adsorption of antigens to a given adjuvant [1,2].

Typically, protein-based vaccine formulations are produced as suspensions or emulsions, the consequence of the inclusion of adjuvants such as aluminum salts (i.e., AlOOH, $AlPO_4$, etc.) or squalenes emulsions (i.e., squalene AS03, MF59, etc.). While adjuvants are often a key component of vaccine formulations [3-5], the presence of adjuvants can produce significant interference with commonly used methods for protein quantification, due to turbidity introduced by the adjuvant particles, for example. Many methods have been published for analysis of antigens present in vaccine formulations containing aluminum salts, but such methods necessitate antigen desorption prior to testing due to the turbidity of the formulations [6-8]. Desorption procedures described in the literature are rather complex and time-consuming, with variable recovery and questionable reproducibility [9,10]. Other methods reported for the quantification of antigens in adjuvanted vaccines, such as flow cytometry [11], chemiluminescent nitrogen detection [12], micro-Kjeldalh [13] and o-phthalaldehyde assays [9], can be directly applied to suspensions. Nevertheless, these methods are mostly destructive, also requiring specific antibodies or special reagents, and therefore they are not suitable for fast turnaround or in-line process monitoring. Currently, there are also no in-line methods for measurement of percent adsorption of adjuvanted vaccine formulations.

It is evident that new nondestructive methods for accurately and reproducibly determining the concentration of adjuvanted antigen in vaccine formulations are needed.

BRIEF SUMMARY OF INVENTION

The present invention relates to novel methodologies designed to overcome the problems associated with accurately and reproducibly determining the concentration of antigen in a vaccine formulation comprising adjuvanted antigen. The methods described herein overcome such problems as the interference of turbidity in samples of adjuvanted antigen in vaccine formulations under evaluation. The methods described herein are based on the discovery by the inventors that the intrinsic fluorescence (IF) of proteins can be measured and quantified when antigens are formulated with adjuvants.

As reported herein, the intrinsic fluorescence of proteins containing certain aromatic amino acids can be used to measure their concentration in most mixtures, even those containing aluminum salt adjuvants, without the need for desorption of the proteins from the adjuvants. This discovery has been extended to the accurate measurement of formulations of selected compounds using intrinsic fluorescence, where the formulations comprise adjuvanted complexes of the selected compounds and where the selected compounds comprise at least one aromatic amino acid.

The invention is briefly summarized in the following paragraphs as including, but not limited to, several embodiments and specific aspects thereof.

Thus, and in a first embodiment, the invention is directed to methods for determining the concentration of a selected compound in a composition comprising an adjuvanted complex of the selected compound. In this embodiment, the method comprises (a) obtaining a fluorescence intensity value for a composition comprising an adjuvanted complex of a selected compound, wherein the selected compound includes at least one aromatic amino acid, and wherein the composition is excited at a wavelength of between 250 and 300 nm, and emission spectrum is determined at a wavelength of between 300 and 500 nm to obtain the fluorescence intensity value for the composition; and (b) comparing the fluorescence intensity value obtained in (a) with a calibration curve prepared using fluorescence intensity values of at least three calibration samples comprising different known concentrations of a representative compound that is representative of the selected compound to thereby determine the concentration of the selected compound in a composition comprising an adjuvanted complex of the selected compound.

In certain aspects of this embodiment, the calibration curve of (b) is prepared using at least three calibration samples comprising different known concentrations of the representative compound, wherein the representative compound in the calibration samples is excited at a wavelength of between 250 and 300 nm, and wherein emission spectra are determined at a wavelength of between 300 and 500 nm for each of the calibration samples.

In certain aspects of this embodiment, the calibration curve of (b) is prepared using at least five calibration samples comprising different known concentrations of the representative compound.

In certain aspects of this embodiment, the calibration curve of (b) is prepared by (a) preparing at least five calibration samples of the representative compound having concentrations representing about 50%, 75%, 100%, 125% and 150% of the suspected concentration of the selected compound in the composition comprising an adjuvanted complex of the selected compound; (b) exciting each calibration sample of (a) using a wavelength of between 250 and 300 nm; (c) determining emission spectra of each sample of (b) using a wavelength of between 300 and 500 nm that produces maximum fluorescence intensity for each calibration sample; (d) plotting values of fluorescence intensity, at the wavelengths of (c) that produced the maximum fluorescence intensity, against the concentration of the representative compound in the calibration samples, thereby preparing a calibration curve of the representative compound.

In certain aspects of this embodiment, the various methods are practiced using an excitation wavelength of between 280 and 290 nm, and the emission spectra are determined at a wavelength of between 320 and 360 nm.

In a second embodiment the invention is directed to methods for determining percent (%) adsorption of a selected compound in a composition comprising an adjuvanted complex of the selected compound. In this embodiment, the method comprises (a) obtaining two test samples of a composition comprising an adjuvanted complex of a selected compound, wherein the selected compound includes at least one aromatic amino acid, and wherein in the first test sample the adjuvanted complex is substantially in solution and wherein in the second test sample the adjuvanted complex is substantially settled out of solution;

(b) determining the concentration of the selected compound in the first test sample via (i) obtaining a fluorescence intensity value for the first test sample wherein the first test sample is excited at a wavelength of between 250 and 300 nm, and emission spectrum is determined at a wavelength of between 300 and 500 nm to obtain the fluorescence intensity value for the first test sample, and (ii) comparing the fluorescence intensity value with a calibration curve prepared using at least three calibration samples comprising different known concentrations of a representative compound that is representative of the selected compound to thereby determine the concentration of the selected compound in the first test sample;

(c) determining the concentration of the selected compound in supernatant of the second test sample via (i) obtaining a fluorescence intensity value for supernatant of the second test sample wherein the supernatant of the second test sample is excited at a wavelength of between 250 and 300 nm, and emission spectrum is determined at a wavelength of between 300 and 500 nm to obtain the fluorescence intensity value for supernatant of the second test sample, and (ii) comparing the fluorescence intensity value with a calibration curve prepared using at least three calibration samples comprising different known concentrations of a representative compound that is representative of the selected compound to thereby determine the concentration of the selected compound in the second test sample; and (d) calculating percent (%) adsorption by dividing the concentration determined in (c) by the concentration determined (b), thereby determining percent (%) adsorption of a selected compound in a composition comprising an adjuvanted complex of the selected compound.

In certain aspects of this embodiment, the calibration curves of (b) and/or (c) are prepared using at least three calibration samples comprising different known concentrations of the representative compound, wherein the representative compound in the calibration samples is excited at a wavelength of between 250 and 300 nm, and wherein emission spectra are determined at a wavelength of between 300 and 500 nm for each of the calibration samples.

In certain aspects of this embodiment, the calibration curves of (b) and/or (c) are prepared using at least five calibration samples comprising different known concentrations of the representative compound.

In certain aspects of this embodiment, the calibration curves of (b) and/or (c) are prepared by (a) preparing at least five calibration samples of the representative compound having concentrations representing about 50%, 75%, 100%, 125% and 150% of the suspected concentration of the adjuvanted complex substantially settled out of solution in the second test sample; (b) exciting each calibration sample of (a) using a wavelength of between 250 and 300 nm; (c) determining emission spectra of each sample of (b) using a wavelength of between 300 and 500 nm that produces maximum fluorescence intensity for each calibration sample; (d) plotting values of fluorescence intensity, at the wavelengths of (c) that produced the maximum fluorescence intensity, against the concentration of the representative compound in the calibration samples, thereby preparing a calibration curve of the representative compound.

In certain aspects of this embodiment, the various methods are practiced using an excitation wavelength of between 280 and 290 nm, and the emission spectra are determined at a wavelength of between 320 and 360 nm.

In certain aspects of this embodiment, the calibration curves of (b) and (c) are the same calibration curve.

In a third embodiment the invention is directed to methods for manufacturing a composition comprising an adjuvanted complex of a selected compound. In this embodiment, the method comprises a step of determining the concentration of a selected compound in a batch of an adjuvanted complex of the selected compound using a method defined in the present application (such as the method of the first embodiment summarized above and described in detail below), and formulating a composition incorporating the batch of the adjuvanted complex of the selected compound on the basis of the results of the determination.

In relevant embodiments and aspects of the invention, the selected compound may be, but is not limited to, a peptide, polypeptide, protein, polysaccharide-protein conjugate, virus-like particle or viral suspension. In one aspect, the selected compound is a protein.

In relevant embodiments and aspects of the invention, the aromatic amino acid may be, but is not limited to, one or more of tryptophan, tyrosine, and phenylalanine.

In relevant embodiments and aspects of the invention, the selected compound is adjuvanted with one or more adjuvants selected from, but not limited to, an aluminum salt, an emulsion, a peptide, a nucleic acid, and a combination of the aforementioned compounds. In one aspect, the adjuvant is an aluminum salt, such as AlOOH or $AlPO_4$.

In relevant embodiments and aspects of the invention, the adjuvant exhibits fluorescence of less than 20% in the range of 290-450 nm when excited with light in a wavelength range of between 280 and 290 nm.

In relevant embodiments and aspects of the invention, intrinsic fluorescence of the selected compound is determined. In one aspect, intrinsic fluorescence of the selected compound is determined in the absence of an added fluorescing probe or marker. In another aspect, the fluorescence intensity value is obtained via a fluorescence probe bound to the selected compound.

In relevant embodiments and aspects of the invention, the selected compound has an emission maximum of between about 320 and 360 nm.

In relevant embodiments and aspects of the invention, the representative compound may be identical to the selected compound or different from the selected compound. For example, when the representative compound is a peptide or protein, it may have at least 90% sequence identity to the selected compound.

In relevant embodiments and aspects of the invention, the representative compound is an adjuvanted complex of the representative compound. The adjuvant may be the same adjuvant used in the production of the adjuvanted complex of the selected compound or a different adjuvant.

In relevant embodiments and aspects of the invention, the fluorescence intensity value is obtained via a fluorescence probe attached to a flow cell, via a photometer.

In relevant embodiments and aspects of the invention, the method is performed in-line, on-line or off-line.

Fourth, fifth, and sixth embodiments of the present invention are directed to systems that can be implemented to perform the methods of the first, second, and third embodiments of the present invention.

In certain aspects of these embodiments, the systems include a computer having a non-transitory memory storing a program, which when executed performs part or all the features of the methods of the present invention.

In certain aspects of these embodiments, the non-transitory memory can be a computer-readable medium such as a semiconductor memory, compact disc read-only memory (CD-ROM), digital video disc (DVD), Blu-ray disc, or other electronic or optical memory device. Additionally, the program is a computer program including executable instructions or one or more algorithms for instructing the computer to perform part or all the features of the methods of the present invention.

In certain aspects of these embodiments, the computer includes a controller that can be implemented as a general purpose processor, central processing unit (CPU), a specialized processor, a field programmable gate array (FPGA), reconfigurable processor, an integrated circuit (IC), application-specific integrated circuit (ASIC), or large scale integrated circuit (LSI) implemented to perform part or all the features of the methods the present invention.

In certain aspects of these embodiments, the systems determine the concentration of a selected compound in a composition comprising an adjuvanted complex of the selected compound, and determine a percent (%) adsorption of a selected compound in a composition comprising an adjuvanted complex of the selected compound.

In certain aspects of these embodiments, the systems include (i) a conveying means, and (ii) a fluorescence intensity value determining means.

In certain aspects of these embodiments, the conveying means, e.g. a tube, conveys a composition comprising an adjuvanted complex of a selected compound or a test sample to the fluorescence intensity value determining means. Additionally, the fluorescence intensity value determining means determines the fluorescence intensity value of the composition. In some aspects, the fluorescence intensity value determining means is a fluorescence probe attached to a flow cell through which the composition or test sample flows via the conveying means. The fluorescence probe may be in communication with a photometer for determining fluorescence intensity values.

In certain aspects of these embodiments, the computer receives fluorescence intensity values and compares these values to the calibration curves, to thereby determine the concentration of the selected compound in a composition comprising an adjuvanted complex of the selected compound.

In certain aspects of these embodiments, the computer receives fluorescence intensity values and compares these values to the calibration curves, to thereby determine percent (%) adsorption of a selected compound in a composition comprising an adjuvanted complex of the selected compound.

The foregoing has outlined rather broadly the features and technical advantages of the present invention in order that the detailed description of the invention that follows may be better understood. Additional features and advantages of the invention will be described herein, which form the subject of the claims of the invention. It should be appreciated by those skilled in the art that any conception and specific embodiment disclosed herein may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that any description, figure, example, etc. is provided for the purpose of illustration and description only and is by no means intended to define the limits the invention.

DETAILED DESCRIPTION OF THE INVENTION

I. Definitions

Figure 1:
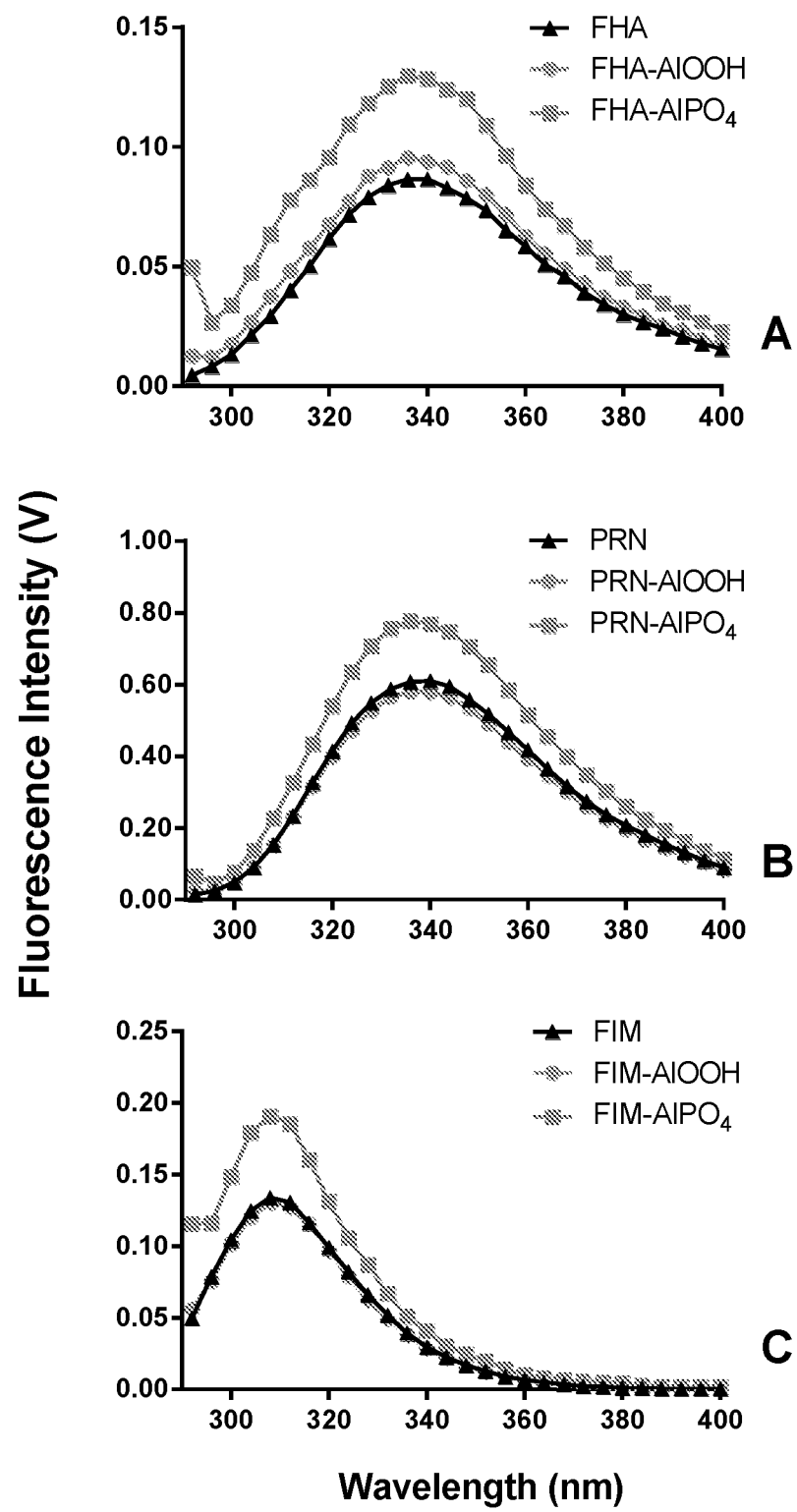
FIG. 1. Fluorescence spectra of FHA (A), PRN (B) and FIM (C), at 100 μg/mL in the absence, or presence, of 0.66 mg Al/mL aluminum salt adjuvant.

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

II. The Present Invention

The present invention is generally directed to the use of the intrinsic fluorescence of a compound, such as a protein, to quantify the concentration of the compound in a solution. By using the linear relation between fluorescence intensity and protein concentration, the fluorescence intensity of a solution of unknown concentration can be assayed and compared to a calibration curve prepared based on the fluorescence intensity of known amounts of the protein.

Proteins are unique among biomolecules in displaying intrinsic fluorescence due to the presence of aromatic amino acids. Most proteins contain aromatic amino acids such as tryptophan (Trp), tyrosine (Tyr), and phenylalanine (Phe). Upon excitation in the UV region (~250 nm for Phe; ~275 nm Tyr; ~290 nm for Trp), these aromatic amino acids can produce an emission spectrum with maximum emission in the range of 310 to 360 nm [14]. The intensity of the emission spectrum is proportional to the number of aromatic amino acids available in solution, and therefore proportional to the concentration of protein in the solution being examined. Amongst the three fluorescent amino acids found in proteins, the contribution of Phe to intrinsic fluorescence of a selected protein is negligible, due to low quantum yield. Although Trp and Tyr possess similar quantum yields, the indole group of Trp has been reported to be the dominant source of UV absorbance near 280 nm and fluorescence emission near 350 nm in proteins [15]. Despite the relatively inferior fluorescence properties of Tyr, analysis of its intrinsic fluorescence has been shown to be a useful tool for analysis of proteins lacking Trp [16].

As discussed herein, it was discovered that the use of intrinsic fluorescence to measure protein concentrations in solutions can be applied to the accurate measurement of complicated solutions comprising components in addition to proteins. This discovery allowed the inventors to overcome difficulties associated with the quantification of protein antigens in vaccine formulations comprising additional components, such as adjuvants. Vaccine formulations comprising an adjuvanted protein are often difficult to assay because such formulations are generally turbid. Accurate measurement of proteins antigens in such formulations has typically required a protein desorption step, a time-consuming and destructive process. The methods of the present invention do not include a protein desorption step to achieve accurate measurement of protein antigens in vaccine formulations. As shown herein, the intrinsic fluorescence of proteins containing aromatic amino acids can be used to measure their concentration in most mixtures, even those containing aluminum salt adjuvants, without the need for desorption.

As briefly summarized above, the invention includes methods for determining the concentration of a selected compound, such as a protein, in a composition comprising an adjuvanted complex of the selected compound. Such methods generally comprise (i) measuring the intrinsic fluorescence of the composition and (ii) comparing the measured fluorescence intensity value to a calibration curve prepared using known concentrations of a compound that is representative of the selected compound, to thereby determine the concentration of the selected compound in the composition. As will be apparent, the invention also encompasses additional methodologies that are based on the steps of (i) measuring the intrinsic fluorescence of a composition and (ii) comparing the measured fluorescence intensity value to a calibration curve.

The methods of the invention explicitly exclude a step of desportion. That is, the methods of the present invention may be practiced by excluding a step of separating the adjuvant from the selected compound in the compositions comprising adjuvanted complexes of the selected compound. The methods of the invention may also be practiced in the absence of an exogenous fluorescent probe or marker. The methods of the invention may further be practiced in the absence of assay conditions that result in the destruction of the adjuvanted complexes of the selected compound and/or the destruction of the selected compound.

As used herein, the term "selected compound" refers to the compound that is being analyzed in the methods of the invention. The selected compound will generally be a compound that comprises at least one aromatic amino acid, for example, a peptide, a polypeptide, or a protein that comprises at least one aromatic amino acid. However, in one alternative the selected compound may be a compound that is bound to or by a compound that comprises at least one aromatic amino acid, for example, a protein lacking an aromatic amino acid that is bound to a protein (e.g., an antibody or fragment thereof) that comprises at least one aromatic amino acid. In a further alternative, the selected compound may be bound to or by a fluorescent probe or marker.

Thus, and as used herein, a selected compound is one or more of (i) a peptide, polypeptide, protein, polysaccharide-protein conjugate, virus-like particle or viral suspension that comprises at least one aromatic amino acid, or (ii) a peptide, polypeptide, protein, polysaccharide-protein conjugate, virus-like particle or viral suspension that does not comprise at least one aromatic amino acid but that is bound to or by (a) a peptide, polypeptide, protein, polysaccharide-protein conjugate, virus-like particle or viral suspension that comprises at least one aromatic amino acid or (b) a fluorescent probe or marker. In one aspect, the selected compound is a protein that comprises at least one aromatic amino acid.

The number of aromatic amino acids in the selected compounds of the invention will vary depending on the identity of the selected compound. As such, the selected compounds of the invention may comprise at least 1, 2, 3, 4, 5, 6, 7, 8, 9, 10 or more aromatic amino acids.

As used herein the term "aromatic amino acids" refers to the amino acids tryptophan (Trp), tyrosine (Tyr), phenylalanine (Phe), histidine (His), thyroxine, 5-hydroxytryptophan, and L-DOPA. In one aspect, the aromatic amino acids can be defined by a subgroup consisting of tryptophan (Trp), tyrosine (Tyr), phenylalanine (Phe).

In those circumstances where the selected compound is bound to or by a fluorescent probe or marker, the fluorescent probe or marker may be any that produces a fluorescence that can be detected and measured in the context of an adjuvanted complex of the selected compound bound to or by the fluorescent probe or marker.

The selected compound may also be characterized, alone or in addition to the other descriptions provided herein, as having an emission maximum of between about 300 and 500 nm, when exposed to an excitation wavelength of between 250 and 300 nm. For some selected compounds, the emission maximum is between about 300 and 450 nm, 300 and 400 nm, 300 and 380 nm, 300 and 370 nm, 300 and 360 nm, 300 and 340 nm, 320 and 400 nm, 320 and 380 nm, or 320 and 360 nm.

As used herein, the term "representative compound" refers to a compound that is used in the production of the calibration curves defined herein. It will be evident that the calibration curves can be constructed using calibration samples that comprise the selected compound being assayed in the method being practiced. Under such circumstances, the representative compound is identical to the selected compound. However, it should also be understood that the calibration curves can be constructed using calibration samples that comprise a compound that is only similar to the selected compound. For example, when a protein is being assayed as the selected compound, a protein having a non-identical sequence can be used as the representative compound in the construction of the calibration curve. When the representative compound is not identical to the selected compound, the representative compound will typically comprise the same complement of aromatic amino acids (both in number and identity) as the selected protein, but this can also vary where the representative compound has fewer or more aromatic amino acids, or different aromatic amino acids. Representative compounds will have at least 80% sequence identity to the selected compound, when the selected compound is a peptide, polypeptide, or protein, or at least 81%, 82%, 83%, 84%, 85%, 86%, 87%, 88%, 89%, 90%, 91%, 92%, 93%, 94%, 95%, 96%, 97%, 98%, or 99% sequence identity to the selected compound.

When used in the methods of the invention, the representative compound may be an adjuvanted complex of the representative compound or a non-adjuvanted version of the representative compound. When the representative compound is adjuvanted, it may be adjuvanted with the same adjuvant used in the production of the adjuvanted complex of the selected compound or a different adjuvant.

As used herein, the term "adjuvant" has its ordinary and customary meaning in the field of vaccine production, e.g. a substance, such as a pharmacologic or immunologic agent, that enhances the immune response of a subject to an antigen. Adjuvants are often included in vaccine formulations to augment the immune response to an antigen that is induce in a subject, thus minimizing the amount of foreign material being administered to the subject. Adjuvants can serve as a depot for the antigen, allowing slow and constant presentation of the antigen to the immune system over time. Other adjuvants act to engage and amplify the immune response that develops in the subject in conjunction with that induced by the antigen.

Suitable adjuvants for use in the methods of the invention include inorganic compounds such as aluminum salts, squalene emulsions, peptides, nucleic acids, mineral oils, synthetic and natural phospholipids, and combinations thereof. Exemplary adjuvants for use in the methods include aluminum hydroxide adjuvant (also referred to as aluminum oxyhydroxide or AlOOH), aluminum phosphate (e.g. $AlPO_4$), amorphous aluminum hydroxyphosphate sulfate and calcium phosphate hydroxide. Exemplary emulsions for use in the methods include squalene AF03 emulsion, MF59®, AS03, Montanide®. Exemplary peptides for use in the methods include peptide-oligonucleotide particulate complexes (e.g., IC31). Exemplary nucleic acids for use in the methods include ODN1a, CpG1018.

In one aspect of the invention, suitable adjuvants will be those that exhibit undetectable intrinsic fluorescence in the range of 290-450 nm when excited with light in a wavelength range of between 250 and 300 nm. Alternatively, suitable adjuvants will be those that exhibit intrinsic fluorescence in the range of 290-450 nm when excited with light in a wavelength range of between 250 and 300 nm that is less than 20% of the intrinsic fluorescence of the selected compound complexed with the adjuvant, preferably less than 20%, 19%, 18%, 17%, 16%, 15%, 14%, 13%, 12%, 11%, 10%, 9%, 8%, 7%, 6%, 5%, 4%, 3%, 2%, or 1% of the intrinsic fluorescence of the selected compound complexed with the adjuvant. In some aspects, the excitation wavelength is between 280 and 290 nm.

The methods of the invention may be practiced using compositions where the selected compound is complexed with one type of adjuvant, or two, three, four or more types of adjuvants in the same composition.

As used herein, the term "composition" may be any composition that comprises an adjuvanted complex of a selected compound. Non-limiting examples include vaccine formulations comprising adjuvanted antigen, such as a peptide complexed to AlOOH or $AlPO_4$.

Turning to the methods of the invention, and as noted above, in a first embodiment the invention can be defined as methods for determining the concentration of a selected compound, such as a protein, in a composition comprising an adjuvanted complex of the selected compound. Such methods generally comprise (i) measuring the intrinsic fluorescence of the composition and (ii) comparing the measured fluorescence intensity value to a calibration curve prepared using known concentrations of a compound that is representative of the selected compound, to thereby determine the concentration of the selected compound in the composition.

As an example, a method encompassed by this embodiment can be described as a method for determining the concentration of a selected compound in a composition comprising an adjuvanted complex of the selected compound, comprising:

(a) obtaining a fluorescence intensity value for a composition comprising an adjuvanted complex of a selected compound, wherein the selected compound includes at least one aromatic amino acid, and wherein the composition is excited at a wavelength of between 250 and 300 nm, and emission spectrum is determined at a wavelength of between 300 and 500 nm to obtain the fluorescence intensity value for the composition; and (b) comparing the fluorescence intensity value obtained in (a) with a calibration curve prepared using fluorescence values of calibration samples comprising different known concentrations of a representative compound that is representative of the selected compound to thereby determine the concentration of the selected compound in a composition comprising an adjuvanted complex of the selected compound.

In certain aspects of this embodiment, the calibration curve of (b) is prepared using at least 2, 3, 4, 5, 6, 7, 8, 9, 10 or more calibration samples comprising different known concentrations of the representative compound. For example, the calibration curve of (b) can be prepared using at least three calibration samples comprising different known concentrations of the representative compound, wherein the representative compound in the calibration samples is excited at a wavelength of between 250 and 300 nm, and wherein emission spectra are determined at a wavelength of between 300 and 500 nm for each of the calibration samples.

In certain aspects of this embodiment, the calibration curve of (b) is prepared using at least five calibration samples comprising different known concentrations of the representative compound, wherein the representative compound in the calibration samples is excited at a wavelength of between 250 and 300 nm, and wherein emission spectra are determined at a wavelength of between 300 and 500 nm for each of the calibration samples.

The concentration of the representative compound in the calibration samples used to prepare a calibration curve will vary depending on the known or suspected concentration of the selected compound and the number of samples used to prepare the curve. However, the calibration samples will general include at least one sample having a concentration below the known or suspected concentration of the selected compound and at least one sample having a concentration above the known or suspected concentration of the selected compound. In some aspects, the calibration samples include 1, 2, 3, 4, 5 or more samples having a concentration below the known or suspected concentration of the selected compound and 1, 2, 3, 4, 5 or more samples having a concentration above the known or suspected concentration of the selected compound. The calibration samples having a concentration below the known or suspected concentration of the selected compound will generally be between about 20 and 100% of the known or suspected concentration of the selected compound, including values of about 20%, 25%, 30%, 35%, 40%, 45%, 50%, 55%, 60%, 65%, 70%, 75%, 80%, 85%, 90%, 95% and 100% of the known or suspected concentration of the selected compound. The calibration samples having a concentration above the known or suspected concentration of the selected compound will generally be between about 100% and 200% of the known or suspected concentration of the selected compound, including values of about 100%, 105%, 110%, 115%, 120%, 125%, 130%, 135%, 140%, 145%, 150%, 155%, 160%, 165%, 170%, 175%, 180%, 185%, 190%, 195% and 200% of the known or suspected concentration of the selected compound.

In certain aspects of this embodiment, the calibration curve of (b) is prepared by (a) preparing at least five calibration samples of the representative compound having concentrations representing about 50%, 75%, 100%, 125% and 150% of the suspected concentration of the selected compound in the composition comprising an adjuvanted complex of the selected compound; (b) exciting each calibration sample of (a) using a wavelength of between 250 and 300 nm; (c) determining emission spectra of each sample of (b) using a wavelength of between 300 and 500 nm that produces maximum fluorescence intensity for each calibration sample; (d) plotting values of fluorescence intensity, at the wavelengths of (c) that produced the maximum fluorescence intensity, against the concentration of the representative compound in the calibration samples, thereby preparing a calibration curve of the representative compound.

The calibration curves used in the methods of the invention may be prepared using any relevant means such as, but are not limited to, computer software, such as Microsoft Excel (Microsoft), JMP (SAS), GraphPad Prism (GraphPad Software), MATLAB (MathWorks), Custom Sensors PX2 (Custom Sensors) and graphing paper (manual drafting). The types of calibrations curve fitting models can vary as well and include, but are not limited to, linear, polynomial, logarithmic, exponential, power, and sigmoidal, regression of the representative compound and concentration range of interest.

As used herein, the "suspected concentration" of the selected compound in the composition comprising an adjuvanted complex of the selected compound is simply an estimate or educated guess as to the concentration of the selected compound in the composition. In order to prepare a relevant calibration curve, one seeks to prepare a curve where the fluorescence intensity value obtained for the composition comprising an adjuvanted complex of a selected compound will fall on the curve somewhere between the lowest and highest values used to prepare the curve. As the fluorescence intensity value of the composition comprising an adjuvanted complex of a selected compound is not known a priori, one must estimate or guess what the value might likely be, and then prepare the calibration curve using samples of the representative compound having concentrations both above and below the estimated value.

Means for accurately measuring the concentration of adjuvanted compounds in a composition can be combined with additional steps that permit one to gather further information about the characteristics of a composition. For example, in a second embodiment the invention includes methods for determining percent (%) adsorption of a selected compound in a composition comprising an adjuvanted complex of the selected compound. Thus, one can determine, for example, the percent of antigen in a vaccine formulation complexed with an adjuvant. Such methods generally comprise (i) obtaining two samples of a composition comprising an adjuvanted complex of a selected compound, where in the first sample the adjuvanted complex is substantially in solution and in the second sample the adjuvanted complex is substantially settled out of solution, (ii) measuring the intrinsic fluorescence of the first sample, (iii) comparing the measured fluorescence intensity value to a calibration curve prepared using known concentrations of a compound that is representative of the selected compound to determine the concentration of the selected compound in the first test sample, (iv) measuring the intrinsic fluorescence of the second sample, (v) comparing the measured fluorescence intensity value to the calibration curve to determine the concentration of the selected compound in the second test sample, and (vi) calculating percent (%) adsorption by dividing the concentration determined for the second sample by the concentration determined for the first sample, to thereby determine percent (%) adsorption of a selected compound in the composition.

As an example, a method encompassed by this embodiment can be described as a method for determining percent (%) adsorption of a selected compound in a composition comprising an adjuvanted complex of the selected compound, comprising:
  (a) obtaining two test samples of a composition comprising an adjuvanted complex of a selected compound, wherein the selected compound includes at least one aromatic amino acid, and wherein in the first test sample the adjuvanted complex is substantially in solution and wherein in the second test sample the adjuvanted complex is substantially settled out of solution;
  (b) determining the concentration of the selected compound in the first test sample via (i) obtaining a fluorescence intensity value for the first test sample wherein the first test sample is excited at a wavelength of between 250 and 300 nm, and emission spectrum is determined at a wavelength of between 300 and 500 nm to obtain the fluorescence intensity value for the first test sample, and (ii) comparing the fluorescence intensity value with a calibration curve prepared using calibration samples comprising different known concentrations of a representative compound that is representative of the selected compound to thereby determine the concentration of the selected compound in the first test sample;

(c) determining the concentration of the selected compound in supernatant of the second test sample via (i) obtaining a fluorescence intensity value for supernatant of the second test sample wherein the supernatant of the second test sample is excited at a wavelength of between 250 and 300 nm, and emission spectrum is determined at a wavelength of between 300 and 500 nm to obtain the fluorescence intensity value for supernatant of the second test sample, and (ii) comparing the fluorescence intensity value with a calibration curve prepared using calibration samples comprising different known concentrations of a representative compound that is representative of the selected compound to thereby determine the concentration of the selected compound in the second test sample; and (d) calculating percent (%) adsorption by dividing the concentration determined in (c) by the concentration determined (b), thereby determining percent (%) adsorption of a selected compound in a composition comprising an adjuvanted complex of the selected compound.

In certain aspects of this embodiment, the calibration curves of (b) and/or (c) are prepared using at least 2, 3, 4, 5, 6, 7, 8, 9, 10 or more calibration samples comprising different known concentrations of the representative compound. For example, the calibration curves of (b) and/or (c) can be prepared using at least three calibration samples comprising different known concentrations of the representative compound, wherein the representative compound in the calibration samples is excited at a wavelength of between 250 and 300 nm, and wherein emission spectra are determined at a wavelength of between 300 and 500 nm for each of the calibration samples.

In certain aspects of this embodiment, the calibration curves of (b) and/or (c) are prepared using at least five calibration samples comprising different known concentrations of the representative compound, wherein the representative compound in the calibration samples is excited at a wavelength of between 250 and 300 nm, and wherein emission spectra are determined at a wavelength of between 300 and 500 nm for each of the calibration samples.

In certain aspects of this embodiment, the calibration curves of (b) and/or (c) are prepared by (a) preparing at least five calibration samples of the representative compound having concentrations representing about 50%, 75%, 100%, 125% and 150% of the suspected concentration of the adjuvanted complex substantially settled out of solution in the second test sample; (b) exciting each calibration sample of (a) using a wavelength of between 250 and 300 nm; (c) determining emission spectra of each sample of (b) using a wavelength of between 300 and 500 nm that produces maximum fluorescence intensity for each calibration sample; (d) plotting values of fluorescence intensity, at the wavelengths of (c) that produced the maximum fluorescence intensity, against the concentration of the representative compound in the calibration samples, thereby preparing a calibration curve of the representative compound.

It will be apparent that the calibration curves of (b) and (c) may be the same calibration curve, or that different calibration curves may be prepared.

In addition, calibration curves may be prepared that take into account the presence of adjuvant remaining in the supernatant of the second test samples after the adjuvanted complexes have substantially settled out of solution. To determine the fluorescence offset caused by the remaining adjuvant in the supernatant after settling, two sets of formulations can be prepared for each representative compound. One set of formulations is made without adjuvant, and the other is made with the concentration of the representative compound expected to remain in the supernatant once settled. The calibration curves of the invention can be revised to take into account the offset value.

In these methods for determining percent (%) adsorption of a selected compound in a composition comprising an adjuvanted complex of the selected compound, two test samples are assayed. In the first test sample the adjuvanted complex is substantially in solution. In the second test sample the adjuvanted complex is substantially settled out of solution and the supernatant is assayed. It will be understood that the amounts of the adjuvanted complex in and out of solution will vary depending on the specific circumstances associated with the assay. Indeed, as the purpose of the assay is to obtain percent (%) adsorption for different compositions, the specific circumstances associated with the assay are expected to vary widely. Therefore, the definitions of the terms "substantially in solution" and "substantially settled out of solution" are necessarily broad. However, the terms can be defined based on a difference of at least about 10% between the amount of adjuvanted complex in the first test sample versus the amount of adjuvanted complex in the supernatant of the second test sample. In other suitable aspects of the invention, there is a difference of at least about 15%, 20%, 25%, 30%, 35%, 40%, 45%, 50%, 55%, 60%, 65%, 70%, 75%, 80%, 85%, 90%, 95% or more between the amount of adjuvanted complex in the first test sample versus the amount in the second test samples. Alternatively, the terms can be defined based on absolute amounts of adjuvanted complex in the test samples. Thus, as used herein the term "substantially in solution" can also mean that at least 51% of the adjuvanted complex is in solution in the sample. In other suitable aspects, at least 55%, 60%, 65%, 70%, 75%, 80%, 85%, 90%, 95% or more of the adjuvanted complex is in solution in the sample. Similarly, as used herein the term "substantially settled out of solution" can also mean that at least 51% of the adjuvanted complex is out of solution in the sample. In other suitable aspects, at least 55%, 60%, 65%, 70%, 75%, 80%, 85%, 90%, 95% or more of the adjuvanted complex is out of solution in the sample. As a further alternative, the first test sample can be defined as a solution of adjuvanted complex that is mixed and subjected to an excitation wavelength within 10, 20, 30, 40, 50, 60, 70, 80, 90, 100, 110 or 120 seconds of mixing. The second test sample can be defined as a solution of adjuvanted complex that is mixed and allowed to remain stationary for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more minutes before the supernatant of the sample is subjected to an excitation wavelength.

It will be apparent that the excitation wavelength used in each of the methods of the invention will vary depending on such factors at the identity of the selected compound, the identity of the representative compound, and the identity of the adjuvant, among other factors. However, as Phe fluoresces at a wavelength of ~250 nm, Tyr fluoresces at a wavelength of ~275 nm, and Trp fluoresces at a wavelength of ~290 nm, the methods of the invention will generally be practiced using an excitation wavelength of between about 250 and 300 nm. Other suitable ranges include between about 250 and 290 nm, 250 and 280 nm, 250 and 270 nm, 250 and 260 nm, 260 and 300 nm, 260 and 290 nm, 260 and 280 nm, 260 and 270 nm, 270 and 300 nm, 270 and 290 nm, 270 and 280 nm, 280 and 300 nm, 280 and 290 nm, and 290 and 300 nm.

It will also be apparent that the emission spectra determined when practicing each of the methods of the invention will vary depending on the same factors, i.e. the identity of the selected compound, the identity of the representative compound, and the identity of the adjuvant, among other factors. However, the methods of the invention will generally be practiced where emission spectra are determined at a wavelength of between 300 and 500 nm. Other suitable ranges include between about 300 and 480 nm, 300 and 460 nm, 300 and 440 nm, 300 and 420 nm, 300 and 400 nm, 320 and 480 nm, 320 and 460 nm, 320 and 440 nm, 320 and 420 nm, 320 and 400 nm, 340 and 480 nm, 340 and 460 nm, 340 and 440 nm, 340 and 420 nm, 340 and 400 nm, 360 and 480 nm, 360 and 460 nm, 360 and 440 nm, 360 and 420 nm, 360 and 400 nm, 380 and 480 nm, 380 and 460 nm, 380 and 440 nm, 380 and 420 nm, 380 and 400 nm, 300 and 400 nm, 300 and 380 nm, 300 and 360 nm, 300 and 340 nm, 300 and 320 nm, 320 and 400 nm, 320 and 380 nm, 320 and 360 nm, 320 and 340 nm, 340 and 400 nm, 340 and 380 nm, 340 and 360 nm, 360 and 400 nm, 360 and 380 nm, and 380 and 400 nm.

The methods of the invention may be practiced using any relevant instrument that can generate the desired excitation wavelength of light and detect the resulting emission spectra within the parameters defined herein. Acceptable instruments include a photometer, a fluorometer, and a spectrophotometer.

The methods of the invention may be practiced using any means for generating a calibration curve from the measurements obtained from the calibration samples. Such means include by hand, e.g. using graph paper and a pencil, and electronic means, such as the use of a computer program.

Similarly, the methods of the invention may be practiced using any means for comparing a fluorescence intensity value with a calibration curve. Such means include by hand, e.g. using graph paper and a pencil to plot a fluorescence intensity value on a calibration curve, and electronic means, such as the use of a computer program.

The methods of the invention can be performed in a variety of circumstances. For example, the methods can be performed in small scale operations that take place in a laboratory setting, such as when small batches of a vaccine formulation are being prepared for injection into experimental animals. Samples can be removed from the individual batches and tested using the methods as defined herein. The methods can also be performed in large scale operations such as in an industrial setting when commercial-grade batches of vaccine formulations are being produced for sale. Again, samples can be removed from the individual batches and tested using the methods as defined herein. Under such conditions, the methods are performed "off-line", i.e. samples are tested for antigen concentration or % absorption in a laboratory setting, using a benchtop fluorometer for example.

Figure 6:
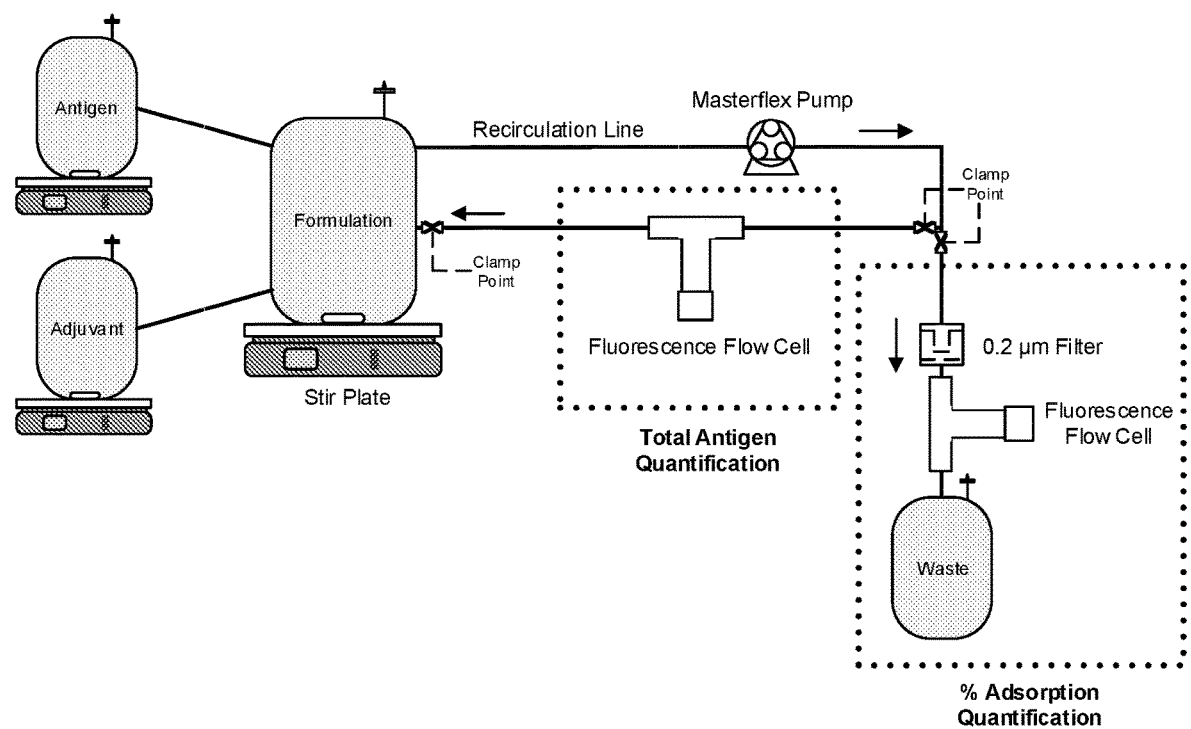
FIG. 6. Concept diagram for the in-line determination of proteins concentration in the presence of adjuvants and at-line determination of antigen % adsorption by intrinsic fluorescence spectroscopy.

The methods can also be performed "in-line" or "on-line" where a fluorescence probe is coupled with a flow cell, that in turn is connected to a photometer, to allow real-time monitoring of protein concentration. The methods can also be performed "in-line" using a fluorescence probe connected to a photometer, and placing the probe into direct contact with the sample (e.g., by dipping probe into sample). FIG. 6 provides an example of using the methods of the invention in determining antigen concentration or % absorption using an on-line set-up. Such in-line and on-line analyses are important for Process Analytical Technology (PAT) applications. PAT is considered by the U.S. FDA as a system for designing, analyzing, and controlling manufacturing through timely measurements (i.e., during processing) of critical quality and performance attributes of raw and in-process materials and processes, with the goal of ensuring final product quality [27].

In relevant embodiments and aspects of the invention, fluorescence values are thus obtained via a fluorescence probe, via a photometer. The fluorescence probe may be attached to a flow cell. Suitable fluorescence probes will be known to those of skill in the art and include, for example, Autoclaveable Front Surface Fluorescence Probe by Custom Sensors, Part #: 3383-001-305-010-2000-101-101. Suitable flow cells will be known to those of skill in the art and include, for example, Thermo Scientific™ Flow Cells for use with autosamplers and sipper systems in a variety of pathlengths, and Single-Use Fluorescence Flow Cells (Prototype) by PendoTECH, Part #: 1161362-210.

As an example, the method of determining the concentration of a selected compound in a composition comprising an adjuvanted complex of the selected compound can be conducted using a fluorescence probe attached to a flow cell, via a photometer (FIG. 6). The fluorescence probe is first calibrated using calibration samples comprising the selected compound or the representative compound in the absence of adjuvant, and a calibration curve is prepared. Then a sample of the adjuvanted formulation is passed into the flow cell and measured for fluorescence. The fluorescence intensity value that is obtained is compared to the calibration curve and the concentration of the selected compound in the composition comprising an adjuvanted complex of the selected compound is determined.

Figure 10:
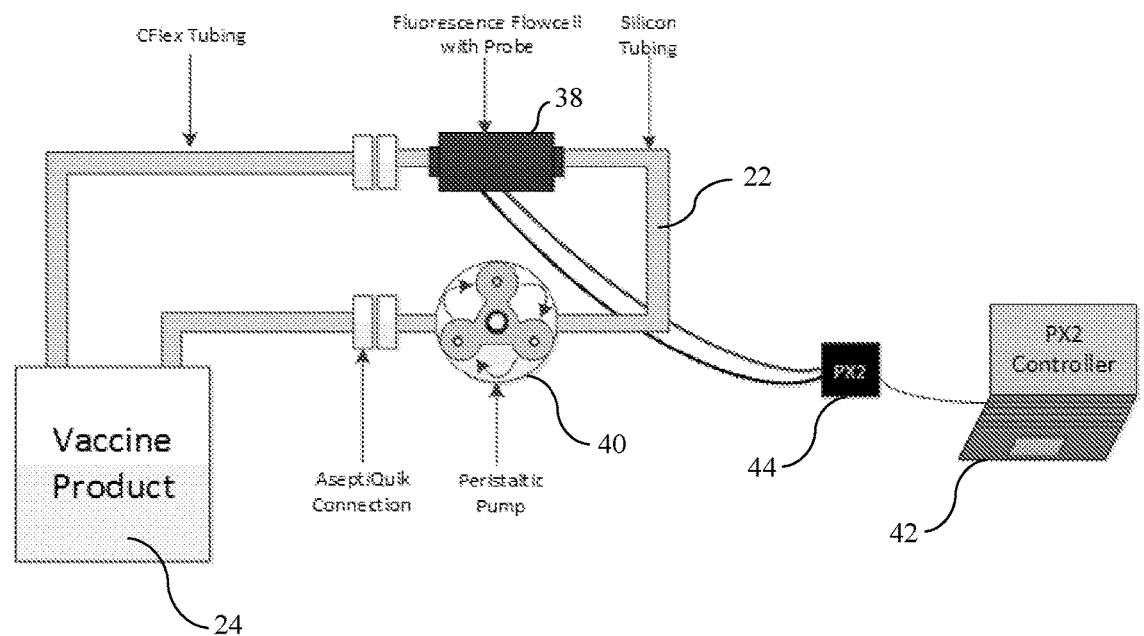
FIG. 10. A schematic diagram of a system for measuring concentration of proteins in a vaccine formulation according to a third exemplary embodiment of a system of the invention.

As a further example, the method of measuring % adsorption of a selected compound to an adjuvant can also be performed using a fluorescence probe attached to a flow cell, via a photometer (FIG. 10). The fluorescence probe is first calibrated using calibration samples comprising the selected compound or the representative compound in the absence of adjuvant. Then a sample of the adjuvanted formulation is passed into the flow cell and measured for fluorescence (as the first test sample where the adjuvanted complex is substantially in solution), the sample is then allowed to rest to let the adjuvanted complex settle out of the flow cell and the sample is again measured for fluorescence of the non-adjuvanted selected compound (as the supernatant of the second test sample where the adjuvanted complex is substantially settled out of solution). An alternative approach of measuring the supernatant uses a filter to remove the adjuvanted complex and the sample is again measured for fluorescence of the non-adjuvanted selected compound (as the supernatant of the second test sample where the adjuvanted complex is substantially settled out of solution) (FIG. 6). The calculation with the two measured values is performed and the % adsorption of the selected compound is thus measured.

The present invention can also be described in a third embodiment. In this embodiment the invention is directed to methods for manufacturing a composition comprising an adjuvanted complex of a selected compound. The method comprises a step of determining the concentration of a selected compound in a batch of an adjuvanted complex of the selected compound using a method defined in the application (such as the method of the first embodiment described in detail herein), and formulating a composition incorporating the batch of the adjuvanted complex of the selected compound proceeds on the basis of the results of the determination.

The present invention also encompasses systems that can be implemented to perform each of the methods of the invention as defined herein.

Figure 8:
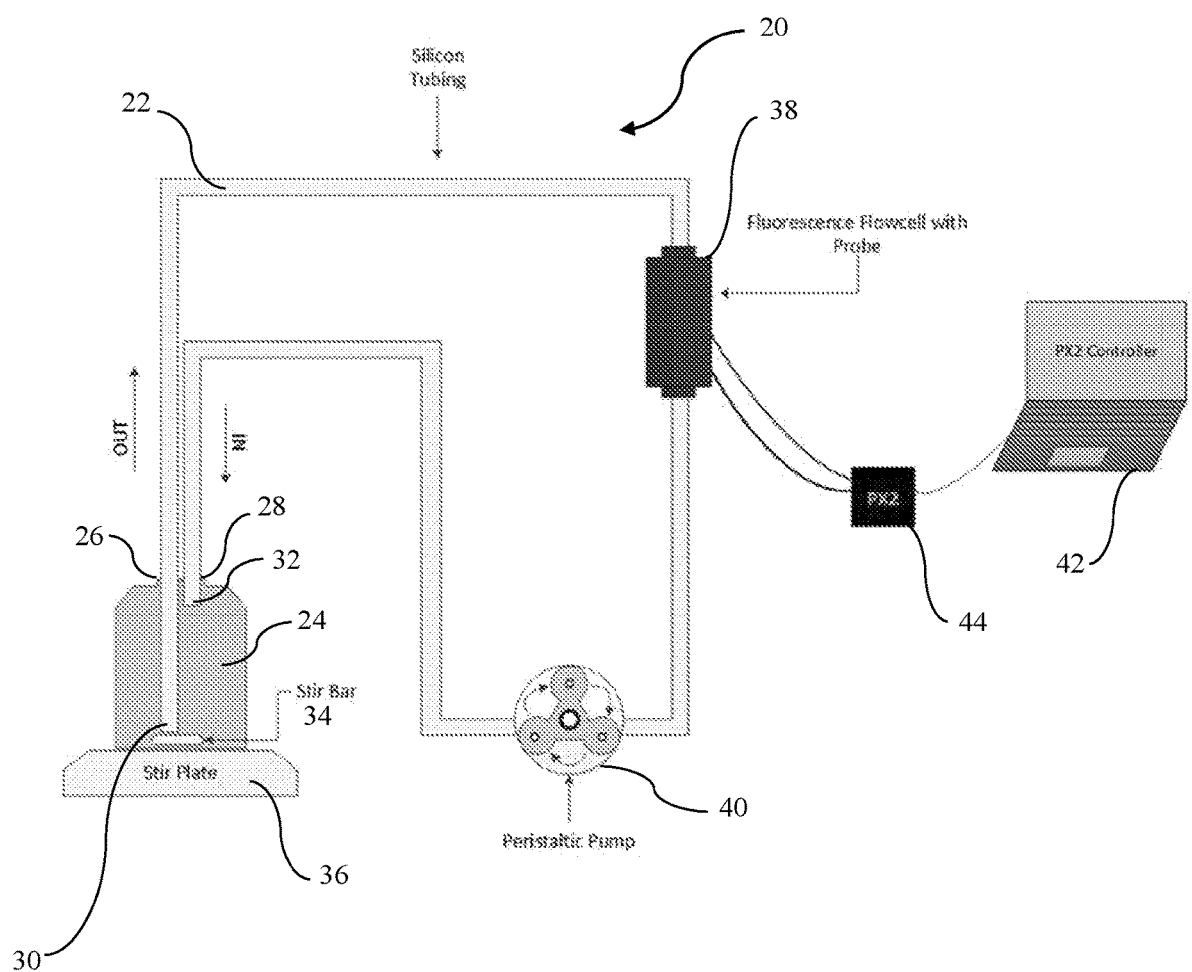
FIG. 8. A schematic diagram of a system for measuring concentration of proteins in a vaccine formulation according to a first exemplary embodiment of a system of the invention.

The system 20 illustrated in FIG. 8 includes a conduit 22 through which a vaccine formulation containing proteins can flow from and return into container 24 having the vaccine formulation therein.

Container 24 has an outlet 26 and an inlet 28 through which the opposite inlet end 30 and the outlet end 32 of conduit 22 extend, respectively. The inlet end 30 is located in container 24 adjacent a stir bar 34 near the container bottom. The container bottom is located on a stir plate 36. The outlet end 32 is located in container 24 adjacent its top. Conduit 22 can comprise flexible or silicon tubing.

Conduit 22 forms a loop with a fluorescence intensity sensor 38 and a pump 40 therein arranged in series between inlet end 30 and outlet end 32, with pump 40 being downstream of sensor 38.

In this manner, the interior of container 24, sensor 38 and pump 40 are in fluid communication. Sensor 38 preferably is a fluorescence flow cell with a probe that measures the fluorescence of the proteins in the vaccine formulation and then generates and issues an electrical signal representative of that fluorescence.

A computer 42 is electrically connected to sensor 38 via a PX2 photometric transmitter device 44 to receive the fluorescence measurement signals from sensor 38. The computer includes a non-transitory memory storing a program comparing the signals representative of fluorescence values of the proteins in the vaccine formulation in the conduit to a calibration curve previously prepared and stored in the computer. The computer then provides an output displaying the concentration of the proteins in the vaccine formulation from the comparison of the signals and the calibration curve.

Figure 9:
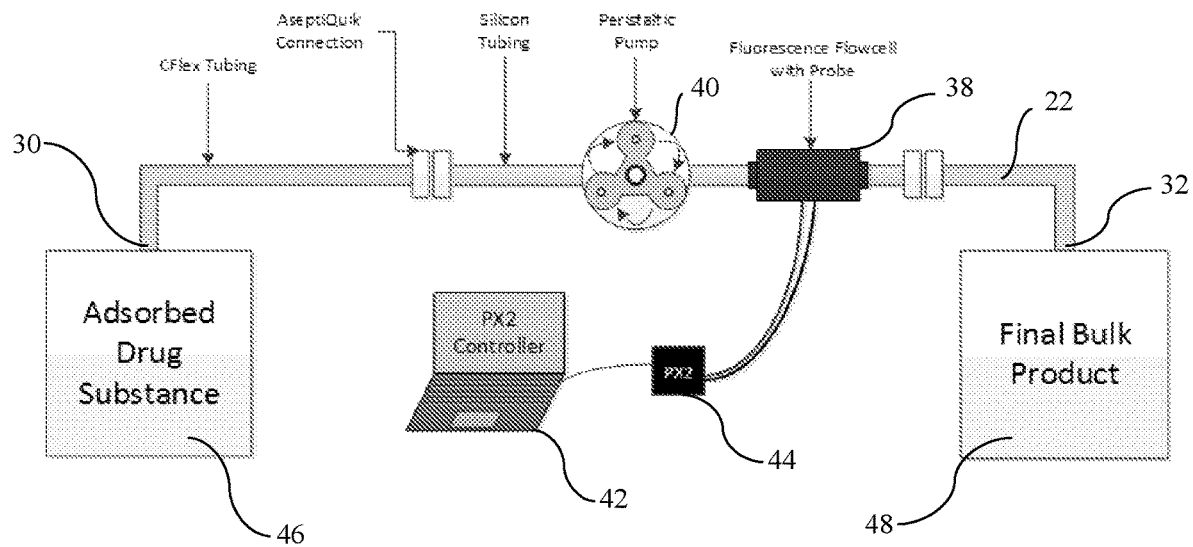
FIG. 9. A schematic diagram of a system for measuring concentration of proteins in a vaccine formulation according to a second embodiment of a system of the invention.

The second exemplary embodiment of FIG. 9 use the same numbers to identify the same features of the first exemplary embodiment of FIG. 8. The main differences between the embodiments of FIG. 8 and FIG. 9 is the open loop of conduit 22, the upstream location of pump 40 relative to sensor 38 and the use of two containers in the FIG. 9 embodiment. Conduit 22 has its inlet end 30 opening into a supply container 46 having an absorbed drug substance therein. The drug substance or a supernatant thereof is drawn from container 46 by pump 40, located upstream from sensor 38 into conduit 22 to and through sensor 38. From sensor 38, the drug substance is conveyed in conduit 22 and exits outlet end 32 into storage container 48 that houses the final bulk product.

The third embodiment of FIG. 10 has a similar arrangement to that of FIG. 8, with like numbers identifying the same parts. The difference is container 24 being generically shown as a blank box.

III. Examples

1A. Materials

Filamentous haemagglutinin (FHA), molecular weight (MW)=220 kDa, Pertactin (PRN), MW=60.3 kDa, Fimbriae (FIM), type 2, MW=19.2 kDa, and type 3, MW=17.2 kDa, were manufactured and provided by Sanofi Pasteur (Toronto, Canada). FHA has 11 tryptophan and 28 tyrosine amino acids, PRN has 8 tryptophan and 6 tyrosine, FIM type 2 has no tryptophan and 8 tyrosine, and FIM type 3 has no tryptophan and 7 tyrosine.

Batches of FHA, PRN and both types of FIM were prepared at concentrations ranging from 973.4-1200.9 μg/mL, 147.7-241.9 μg/mL and 242.0-402.0 μg/mL, respectively. The AlOOH adjuvant was supplied at 10.2 mg Al/mL by Brenntag Biosector (Frederikssund, Denmark). The $AlPO_4$ adjuvant was prepared by Sanofi Pasteur (Toronto, Canada) at 4.1 mg Al/mL. The buffers 10 mM Tris-HCl with 150 mM NaCl pH 7.4 (TBS), phosphate buffered saline (PBS), 150 mM citrate pH 6, 100 mM bicarbonate pH 9, and 0.5 M phosphate pH 7.4, were made in house with reagents supplied by Sigma-Aldrich (Sigma-Aldrich, St. Louis, MO, USA). HEPES was supplied by Life Technologies at 1 M concentrated solution and diluted to 10 mM with Milli-Q water and the pH was adjusted using 1 M HCl.

1B. Preparation of Formulations

All formulations were prepared by adding the appropriate amount of adjuvant to the applicable amount of protein, and then using the designated buffer as a final diluent. Formulations were then mixed on an Adams™ Nutator Mixer (Becton Dickinson, New Jersey, United States) at room temperature for 30 minutes to allow for antigen adsorption to the adjuvant.

Unless stated, the buffer used for the standard curves and test samples was TBS. However, other buffers (PBS, HEPES, citrate, and bicarbonate) were used to test the effect of buffer and pH conditions on the calibration curves. To test the effect of percent adsorption, different concentrations of phosphate (0 mM, 2 mM, 20 mM and 80 mM) were added to the formulations in TBS.

Test samples containing FHA, prepared to assess the effect of adjuvant presence and inter-assay variation on calibration curve accuracy, were prepared at antigen concentrations of 10, 50 and 200 μg/mL, with an adjuvant concentration of 0.66 mg Al/mL for the formulations containing either AlOOH or $AlPO_4$. Test samples containing FHA, created to assess the effect of sedimentation, were prepared at an antigen concentration of 100 μg/mL, with 0.66 mg Al/mL adjuvant concentration for the formulations containing either AlOOH or $AlPO_4$.

Test samples containing PRN, created to assess the effect of adjuvant presence, buffer and pH on calibration curve accuracy, were prepared at antigen concentrations of 10, 50 and 100 μg/mL, with an adjuvant concentration of 0.66 mg Al/mL of adjuvant for the formulations containing either AlOOH or $AlPO_4$.

Test samples containing FIM, prepared to assess the effect of adjuvant presence on calibration curve accuracy, were prepared at antigen concentrations of 10, 50 and 200 μg/mL, with an adjuvant concentration of 0.66 mg Al/mL adjuvant for the formulations containing either AlOOH or $AlPO_4$.

1C. Fluorescence Measurements

Fluorescence measurements of all formulations were collected using Chirascan Plus spectrophotometer (Applied Photophysics, Surrey, United Kingdom). The samples were excited at an excitation wavelength of 280 nm and the emission spectra were collected between 290-400 nm, at 1 nm increments and a measurement time per point of 0.5 seconds, using a constant photomultiplier tube setting of 800 V and a set temperature of 20° C. Once a maximum emission peak was found, the spectra collection was set to ±20 nm from the maximum emission peak. Standard 10 mm quartz cuvettes were used to measure the formulations. Readings were taken immediately after mixing for optimal results.

1D. Sedimentation Study

FHA samples were mixed by 10 repeated inversions, and the fluorescence intensity at 330 nm was collected at 2 minute intervals, for 20 minutes. The fluorescence intensity, at 330 nm, was averaged between the duplicates.

1E. Calibration Curves

The FHA calibration curves created to assess the effect of adjuvant were created with samples at antigen concentrations of 0, 1, 5, 10, 50, 100, 200, 300, 500 and 750 µg/mL, and an adjuvant concentration of 0.66 mg Al/mL for the formulations containing either AlOOH or $AlPO_4$. The FHA calibration curves created to assess the effect of adjuvant concentration were created with samples at antigen concentrations of 5, 10, 50, 100 and 200 µg/mL, and AlOOH or $AlPO_4$ concentrations of 0.33 mg Al/mL, 0.66 mg Al/mL and 1.32 mg Al/mL.

The PRN calibration curves created to assess the effect of adjuvant were created with samples at antigen concentrations of 0, 1, 5, 10, 50 and 100 µg/mL, and an adjuvant concentration of 0.66 mg Al/mL for the formulations containing either AlOOH or $AlPO_4$. The PRN calibration curves created to assess the effect of buffer composition and pH, were created with samples at antigen concentrations of 0, 5, 10, 50 and 100 µg/mL, and an AlOOH concentration of 0.66 mg Al/mL.

The FIM calibration curves created to assess the effect of adjuvant were created with samples at antigen concentrations of 0, 1, 5, 10, 50, 100, 150, 200 and 300 µg/mL, and an adjuvant concentration of 0.66 mg Al/mL for the formulations containing either AlOOH or $AlPO_4$.

The wavelength at which the maximum intensity was reached was selected and the fluorescence at this point was averaged between duplicates and plotted against its concentration. For the calibration curves generated to assess the effect of adjuvant and adjuvant concentration, the fluorescence intensities were averaged between the duplicates. For all other calibration curves, no replicates were obtained. Limit of detection (LOD) and limit of quantification (LOQ) were calculated using the International Council for Harmonization of Technical Requirements for Pharmaceuticals for Human Use (ICH) guidelines [17], as follows:

$$LOD = 3.3\sigma/S$$

$$LOQ = 10\sigma/S$$

σ=standard deviation of the blank
S=slope of the linear regression curve.

Limit of linearity (LOL) was established by removing data points, starting from the highest concentration of antigen, from the calibration curve, until both the $R^2$ of the linear regression was ≥0.980 and the runs test for departure from linearity produced a p-value>0.05, using GraphPad Prism version 6.00 (GraphPad Software, La Jolla California, USA).

Statistical comparison of the linear regression slopes was performed by analysis of covariance (ANCOVA), using GraphPad Prism version 6.00 (GraphPad Software, La Jolla California, USA). Slopes were considered to be statistically different if the probability (p-value) of obtaining a test statistic, F, greater than the one calculated by pure chance was valued at 0.05 or less.

1F. Inter-Assay Variability

Inter-assay variability was investigated by measuring 10 aliquots of test samples, prepared at low (10 µg/mL), medium (50 µg/mL) and high (100 µg/mL) concentrations of FHA adsorbed to 0.66 mg Al/mL AlOOH, against 10 aliquoted calibration curves of FHA-AlOOH formulations.

1G. Percent Adsorption

Percent Adsorption was tested with 50 µg/mL of PRN adsorbed to 0.66 mg Al/mL AlOOH with the presence of 0 mM, 2 mM, 20 mM and 80 mM phosphate to create a difference in the percent adsorption levels. The fluorescence of the total formulations was collected, along with the fluorescence of the supernatant, after centrifugation at 14000 rpm for 10 minutes. The concentration of the formulations, and the supernatant, was back-calculated using their respective standard curves.

1H. Comparison with Micro-Kjeldahl

Samples of unknown antigen concentrations were measured by both micro-Kjeldahl [18] and intrinsic fluorescence (IF) methods. For the IF method, adjuvant-free samples were diluted in TBS, and samples containing $AlPO_4$ were diluted in TBS containing 0.66 mg Al/mL of $AlPO_4$, until a concentration value within the respective calibration curve range was obtained. All dilutions were back calculated using the linear regression of their respective standard curve. The back calculated concentrations were compared against the micro-Kjeldahl results.

2A. Effect of Aluminum Salt Adjuvants on the Fluorescence Spectrum of Protein Antigens To investigate the feasibility of the IF method for the detection of protein concentration in the presence of aluminum salt adjuvants, formulations of FHA, PRN and FIM, at 100 µg/mL, in the presence of AlOOH or $AlPO_4$, were excited at 280 nm and their full emission spectra from 290-400 nm was immediately collected in square 10 mm cuvettes (FIG. 1). In the absence of aluminum salts, both FHA and PRN showed broad and well detectable peaks, with a maximum near 330 nm (FIG. 1A,B), while FIM displayed a narrower peak with maximum fluorescence intensity near 310 nm (FIG. 1C). The lower emission wavelength detected in FIM is attributed to a lack of tryptophan in its structure, making tyrosine the primary contributor to the fluorescence spectrum [19]. The addition of aluminum salts did not significantly affect the maximum emission wavelength. However, the fluorescence intensity was impacted depending on the type of adjuvant used in the formulation. While a significant increase in the fluorescence intensity was observed for $AlPO_4$ containing samples, the presence of AlOOH did not notably impact the fluorescence spectra of the proteins under investigation (FIG. 1).

These results indicate that the presence of aluminum salts at adjuvant concentrations commonly used in vaccines does not interfere with the fluorescence properties of proteins, making this method feasible for the detection of proteins in aluminum salt adjuvanted vaccines.

2B. Effect of Sedimentation

Figure 2:
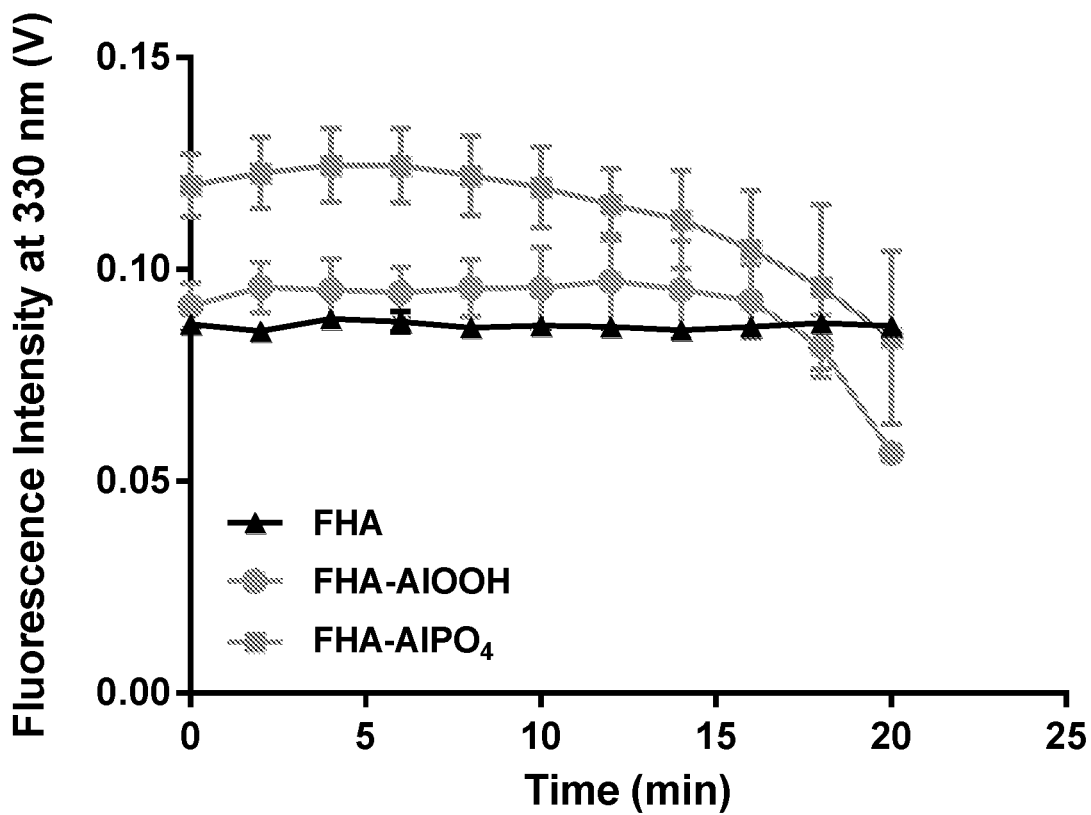
FIG. 2. Fluorescence intensity of antigens alone or adsorbed to adjuvants over time. Fluorescence intensity at 330 nm (280 nm excitation) of 100 μg/mL FHA, and FHA in the presence of 0.66 mg Al/mL AlOOH and $AlPO_4$, at 2 minute intervals, over a period of 20 minutes (n=2). The error bars represent the standard deviation from the mean.

Suspensions of aluminum salt adjuvants are known to sediment over time [20]. To investigate the effect of sedimentation on IF, the fluorescence intensity of formulations containing 100 µg/mL FHA alone, or adsorbed to 0.66 mg Al/mL AlOOH or $AlPO_4$, were measured at 2 minute intervals for a total of 20 minutes. The antigen FHA was selected because it is known to bind to a high extent to both AlOOH and $AlPO_4$ at neutral pH [21]. As expected, the fluorescence intensity of FHA alone showed no changes over time, while a decrease in fluorescence intensity was seen with both aluminum salts (FIG. 2). As the aluminum adjuvants settle, the protein that is bound to the adjuvant gets pulled down below the excitation beam, which caused the observed decrease in fluorescence intensity (FIG. 2). However, the time for which fluorescence intensity was undisturbed varied depending on the adjuvant. Protein adsorbed to $AlPO_4$ was found to settle after about 10 minutes, while in AlOOH, settling started to occur after about 16 minutes (FIG. 2). This is likely due to the differences in the sedimentation rate that can be greatly influenced by particle size, shape, density and the magnitude of zeta potential of the aluminum salts. To address the effect of sedimentation, all further fluorescence measurements were obtained within 2 minutes of mixing samples in the cuvettes.

2C. Calibration Curves

Once detection was proven to be possible in the presence of adjuvants, an investigation of the linear response of fluorescence to protein concentration was conducted. Calibration curves were generated for FHA, PRN and FIM in 0.66 mg Al/mL AlOOH or AlPO$_4$, or in TBS (control), between 1 µg/mL and the highest concentration possible for the protein batch of interest. The slopes of the linear regressions were compared using ANCOVA.

Linear trends can be clearly detected both in the antigen alone and the antigen adsorbed to aluminum salt adjuvants, with correlation coefficients ($R^2$) greater than 0.993 (FIG. 3) (Table 1).

TABLE 1

Coefficient of Determination, LOD and LOQ of Calibration Curves for FHA, PRN and FIM

| Standard curve | $R^2$ | LOD (µg/mL) | LOQ (µg/mL) | LOL (µg/mL) |
|---|---|---|---|---|
| FHA | 1.000 | 1.4 | 4.3 | 200 |
| FHA-AlOOH | 0.996 | 1.5 | 4.4 | |
| FHA-AlPO$_4$ | 0.993 | 1.4 | 4.2 | |
| PRN | 0.999 | 0.2 | 0.6 | 100 |
| PRN-AlOOH | 0.999 | 0.1 | 0.4 | |
| PRN-AlPO$_4$ | 0.994 | 0.3 | 1.0 | |
| FIM | 0.999 | 0.3 | 1.0 | 200 |
| FIM-AlOOH | 0.999 | 1.2 | 3.8 | |
| FIM-AlPO$_4$ | 0.999 | 0.9 | 2.6 | |

For the most part, the addition of adjuvants did result in a slight reduction in the $R^2$ value, specifically for FHA and PRN, which is most likely due to the increased variability brought on by the greater complexity inherent to the adjuvant matrix. Changes in the adjuvant particle size distribution and/or concentration from sample-to-sample in the standard curve would increase variability and have a negative impact on the correlation coefficient.

Limit of detection (LOD) and limit of quantification (LOQ) were determined using the ICH guidelines based on the standard deviation of the blank (Table 1) [17]. PRN formulations were found to have, as a whole, the lowest LOD and LOQ, followed by FIM and FHA. This may be related to the higher molar concentration of the fluorophore Trp in PRN compared to FHA. It is estimated that under identical w/v concentration, PRN samples yield about 2.6 times higher molar concentration of Trp than FHA.

Figure 3:
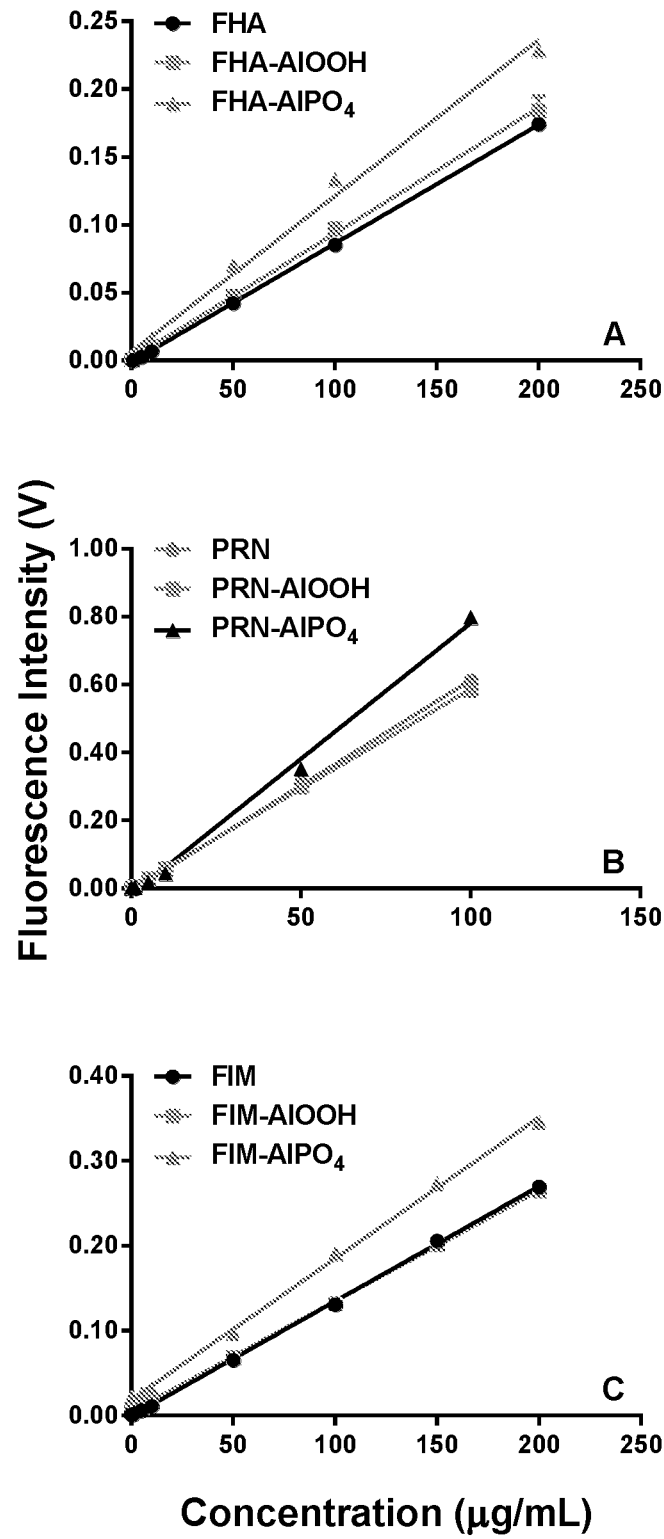
FIG. 3. Calibration curves of FHA (A), PRN (B), FIM (C). Formulations of the antigen alone and adsorbed to 0.66 mg Al/mL of either AlOOH or $AlPO_4$. Upon excitation at 280 nm, the florescence intensity (FHA at 337 nm, PRN at 337 nm and FIM at 310 nm) was plotted against the concentration (n=2). The error bars represent the standard deviation from the mean.

The addition of AlPO$_4$ to the formulations caused a significant increase (p-value<0.0001) in the calibration curve slope for all antigens, indicating an increase in sensitivity (FIG. 3). The addition of AlOOH to the formulations also had a statistically significant effect on the calibration curve slopes, though not to the same extent as AlPO$_4$ in all cases. The AlOOH inclusion in the FHA formulation increased the slope (p-value=0.002), also suggesting an improvement in sensitivity. The presence of AlOOH in PRN and FIM formulation decreased the slope (p-value=0.0007 and p-value<0.0001, respectively), indicating a drop in sensitivity. Therefore, it was established that the calibration curve sensitivity is specific to the antigen-adjuvant combination under consideration.

The limit of linearity (LOL) was calculated as the highest concentration of antigen that produced both an $R^2$>0.980 and a p-value>0.05 for the runs test for departure from linearity, and this was found to be antigen dependent (Table 1). The IF assay was acceptably accurate for the formulations tested. FIM formulations produced the highest overall percent recovery of the test samples, followed by FHA, and then PRN (Table 2). There was no apparent trend regarding percent recovery and test sample concentration or the presence of a specific aluminum salt.

TABLE 2

Accuracy of Calibration Curves for FHA, PRN and FIM

| Formulation | Nominal concentration (µg/mL) | Concentration[a] (µg/mL) | Percent recovery[b] |
|---|---|---|---|
| FHA | 10 | 8.5 | 85.0 |
| | 50 | 50.0 | 100.0 |
| | 200 | 201.0 | 100.5 |
| FHA-AlOOH | 10 | 9.9 | 99.0 |
| | 50 | 47.5 | 95.0 |
| | 200 | 184.6 | 92.3 |
| FHA-AlPO$_4$ | 10 | 9.3 | 93.0 |
| | 50 | 53.5 | 107.0 |
| | 200 | 185.8 | 92.9 |
| PRN | 10 | 7.3 | 73.0 |
| | 50 | 49.3 | 98.6 |
| | 100 | 97.3 | 97.3 |
| PRN-AlOOH | 10 | 10.3 | 103.0 |
| | 50 | 48.1 | 96.2 |
| | 100 | 97.3 | 97.3 |
| PRN-AlPO$_4$ | 10 | 5.8 | 58.0 |
| | 50 | 44.8 | 89.6 |
| | 100 | 93.8 | 93.8 |
| FIM | 10 | 9.9 | 99.0 |
| | 50 | 48.8 | 97.6 |
| | 200 | 201.9 | 101.0 |
| FIM-AlOOH | 10 | 9.8 | 98.0 |
| | 50 | 47.8 | 95.6 |
| | 200 | 196.9 | 98.5 |
| FIM-AlPO$_4$ | 10 | 7.0 | 70.0 |
| | 50 | 47.8 | 95.6 |
| | 200 | 195.0 | 97.5 |

[a]Concentrations were back calculated by using linear regression of the standard curve.
[b]Percent recovery = (calculated concentration/nominal concentration) × 100.

2D. Inter-Assay Variability

Formulations of FHA adsorbed to 0.66 mg Al/mL AlOOH, at low (10 µg/mL), medium (50 µg/mL) and high (100 µg/mL) protein concentrations were used to investigate the inter-assay variability. The coefficient of variation (CV) for low, medium and high concentration samples was 7.4%, 1.5%, and 0.6%, respectively, for all 10 experiments performed, indicating high reproducibility of the IF assay (Table 3).

TABLE 3

Inter-assay variation of FHA-AlOOH calibration curve

| | Intrinsic Fluorescence Determined Concentration[a] | | |
|---|---|---|---|
| Replicate number | 10 µg/mL nominal concentration | 50 µg/mL nominal concentration | 100 µg/mL nominal concentration |
| 1 | 9.1 | 48.5 | 196.6 |
| 2 | 10.6 | 50.6 | 199.8 |
| 3 | 9.9 | 50.1 | 198.2 |
| 4 | 10.6 | 50.0 | 198.0 |
| 5 | 9.9 | 48.8 | 196.7 |
| 6 | 10.7 | 49.2 | 197.8 |
| 7 | 10.3 | 49.2 | 198.1 |
| 8 | 8.5 | 50.2 | 197.1 |
| 9 | 10.4 | 48.5 | 197.4 |

TABLE 3-continued

Inter-assay variation of FHA-AlOOH calibration curve

| | Intrinsic Fluorescence Determined Concentration[a] | | |
|---|---|---|---|
| Replicate number | 10 μg/mL nominal concentration | 50 μg/mL nominal concentration | 100 μg/mL nominal concentration |
| 10 | 9.3 | 49.5 | 200.3 |
| Mean | 9.9 | 49.5 | 198.0 |
| SD[b] | 0.7 | 0.8 | 1.2 |
| CV[c] (%) | 7.4 | 1.5 | 0.6 |

[a]Replicate concentrations were back calculated by using linear regression of the replicate standard curve.
[b]Standard deviation.
[c]Coefficient of variation = (standard deviation/mean) × 100.

2E. Effect of Adjuvant Concentration

To investigate the effect of adjuvant concentration, calibration curves for FHA were prepared at low (0.33 mg Al/mL), medium (0.66 mg Al/mL), and high (1.32 mg Al/mL) adjuvant concentrations and compared using ANCOVA.

Figure 4:
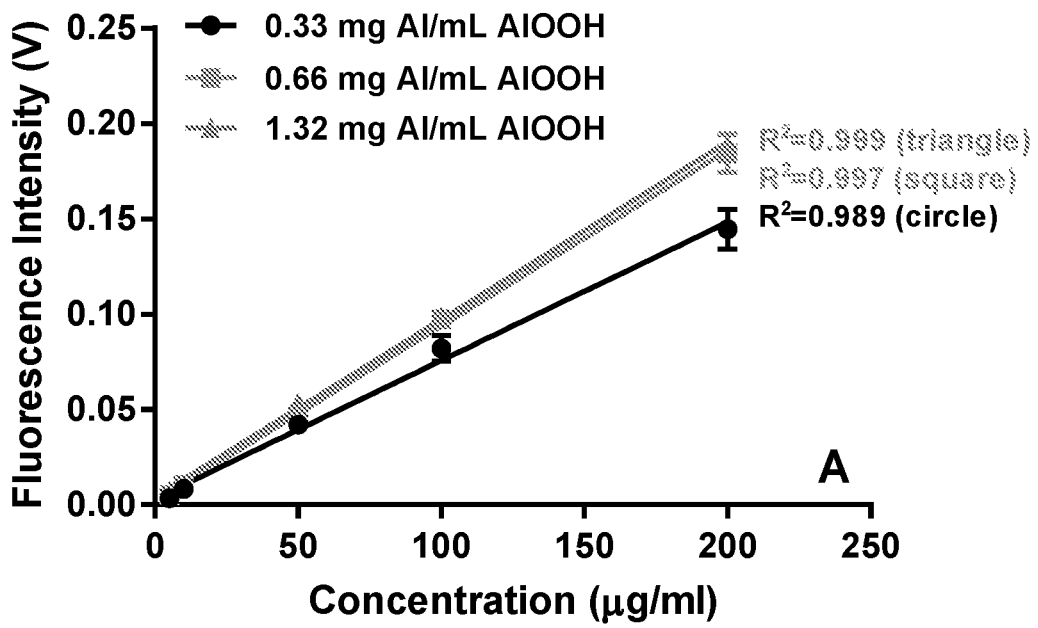
FIG. 4. Calibration curves prepared in low, medium, and high adjuvant concentrations. FHA adsorbed to AlOOH (A) and FHA adsorbed to $AlPO_4$ (B) at 0.32 (low), 0.66 (medium), and 1.32 (high) mg Al/mL Al salt (n=2). The error bars represent the standard deviation from the mean.
Figure 4:
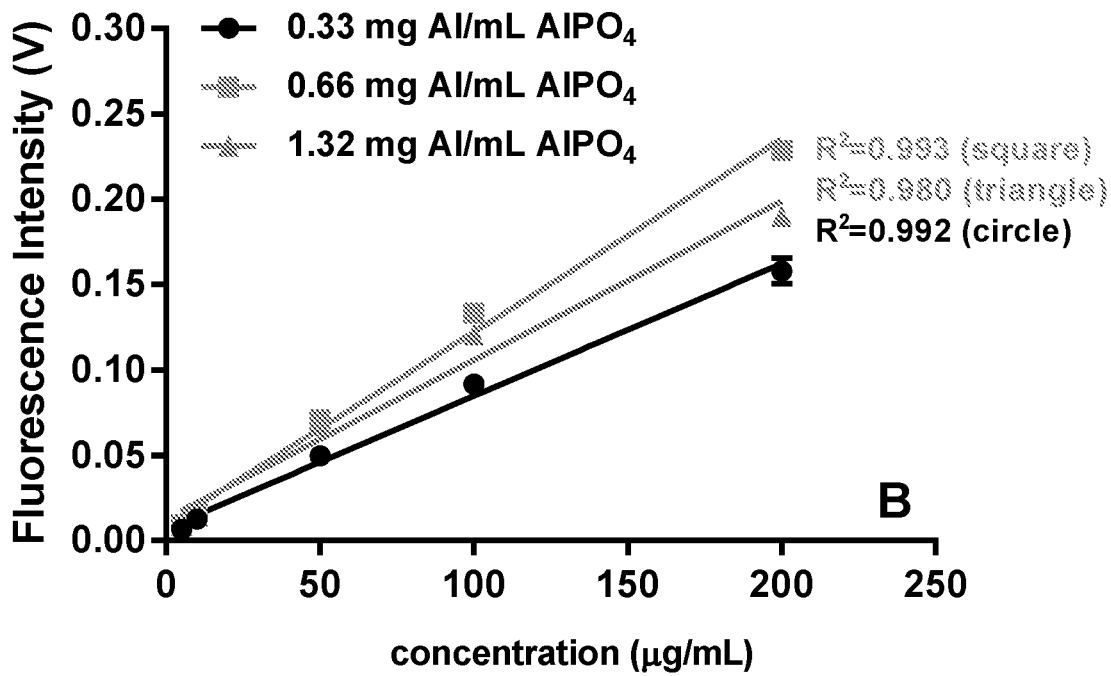

The slopes of the calibration curves changed significantly depending on the concentration of adjuvant, indicating a change in sensitivity (FIG. 4). In the case of AlOOH, at 0.33 mg Al/mL, the calibration curve had a significantly lower slope than the 0.66 mg Al/mL and 1.32 mg Al/mL formulations (p-value<0.0001 for both), though there was no significant difference between the 0.66 mg Al/mL and 1.32 mg Al/mL slopes (p-value=0.6) (FIG. 4A). For $AlPO_4$, an increase in adjuvant concentration from 0.33 mg Al/mL to 0.66 mg Al/mL significantly increased the slope of the calibration curve (p-value<0.0001); however, a further increase to 1.32 mg Al/mL produced a decrease in the slope, though still significantly steeper than that of the 0.33 mg Al/mL curve (p-value=0.01) (FIG. 4B). The $R^2$ value was seen to improve with increasing AlOOH concentration (from 0.989 to 0.999); however, the opposite was obtained for increasing concentrations of $AlPO_4$ (from 0.992 to 0.980). This could be an indication that the increase in $AlPO_4$ content is enhancing the fluorescence closer to the saturation point, perturbing the linearity of the curve. In contrast, the increase in AlOOH concentration may be just enough to provide metal enhanced fluorescence (MEF), while still being below fluorescence saturation.

2F. Effects of Buffers Species and pH

The effect of buffer composition and pH was studied by creating calibration curves of PRN in 0.66 mg Al/mL AlOOH formulated in various buffers species and pHs and compared using ANCOVA.

Figure 5:
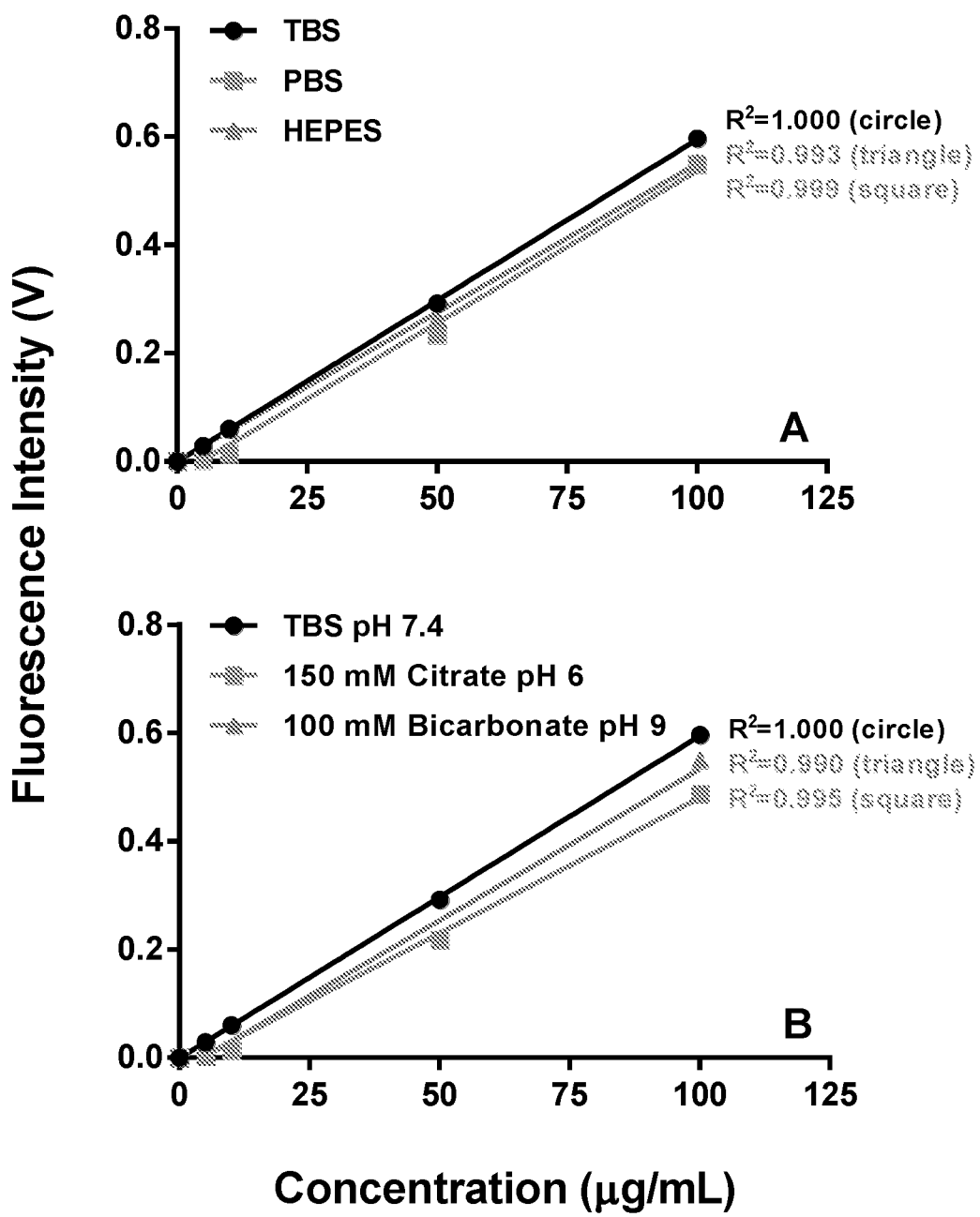
FIG. 5. Effect of buffers and pH on calibration curves. PRN adsorbed to 0.66 mg Al/mL AlOOH calibration curves were made with different buffer compositions and pH. Individual calibration curves for 3 different buffers (TBS, PBS, and HEPES) at a pH of 7.4 (A), and for buffers at 3 different pHs (6, 7.4, and 9) (B).

When different buffer species were compared at neutral pH (FIG. 5A) no significant differences were observed in the slopes (p-value=0.2). However, changing the pH resulted in significant changes in the slope of the calibration curves for PRN-AlOOH formulations (p-value=0.04) (FIG. 5B). These results suggest that calibration curves should match the buffer pH of test samples to ensure accurate determination of antigen concentrations. Where accuracy is of the highest importance, it is recommended that buffer conditions and pH be identical for the test samples and calibration curves. Under certain circumstances, such as sample volume limitations or high throughput needs (i.e., buffer composition pH and ionic strength screening), where accuracy can be leveraged for efficiency or constraints, utilizing a calibration curve of a single buffer condition (or pooling multiple buffer conditions) may be an option.

2G. Percent Adsorption

The percent of antigen adsorption is an important parameter that needs to be adjusted to desired levels during formulation development of vaccines [22]. PRN-AlOOH formulations were used as a model to investigate the utility of the IF method to determine the percent adsorption of antigens to aluminum salt adjuvants. To obtain different levels of adsorption, the AlOOH was pretreated with different amounts of phosphate ions. When the concentration of phosphate ions was increased from 0 to 80 mM, a significant increase in the concentration of unbound PRN was detected by IF assay (Table 4), which translated to a decreased percentage of adsorption from 67 to 7.6%. A small decrease in the total antigen concentration was detected in samples treated with phosphate, which may suggest some impact of either the degree of PRN adsorption or phosphate concentration on the quantification of PRN by IF.

TABLE 4

Determining percent adsorption using intrinsic fluorescence of 50 μg/mL (nominal) PRN in AlOOH

| Phosphate concentration (mM) | Total PRN Concentration (μg/mL)[a] | Recovery[b] (%) | Concentration of Supernatant (μg/mL)[c] | Adsorption[d] (%) |
|---|---|---|---|---|
| 0 | 48.4 | 96.8 | 15.9 | 67.2 |
| 2 | 42.3 | 84.5 | 31.3 | 26.0 |
| 20 | 42.6 | 84.9 | 38.9 | 8.4 |
| 80 | 42.2 | 84.4 | 39.0 | 7.6 |

[a]Concentrations were back calculated by using linear regression of the PRN-AlOOH (0.66 mg Al/mL) standard curve.
[b]Percent recovery = (calculated concentration/nominal concentration) × 100.
[c]Concentrations were back calculated by using linear regression of the PRN standard curve.
[d]Fraction adsorbed is the percent of PRN adsorbed to the adjuvant. Fraction adsorbed = (|concentration of total formulation − concentration of supernatant|/concentration of total formulation) × 100.

2H. Comparison with Micro-Kjeldahl.

The IF method was compared against the micro-Kjeldahl technique. This elemental analysis technique determines protein concentration through quantification of organic nitrogen and can be applied to both adjuvanted and non-adjuvanted samples. Samples of unknown antigen concentration (both adjuvanted and unadjuvanted) were measured by micro-Kjeldahl and IF. The percent difference across batches for FHA, PRN, FHA-$AlPO_4$ and PRN-$AlPO_4$ was 0.0-16.0%, 2.7-7.1%, 9.0-14.1% and 3.2-6.6%, respectively (Table 5). The results for both adjuvant and non-adjuvanted formulations indicated a very good agreement among micro-Kjeldahl and IF methods (Table 5).

TABLE 5

Testing the accuracy of intrinsic fluorescence against micro-Kjeldahl for determining protein concentration in adjuvants

| Antigen | Adjuvant | Lot | Intrinsic Fluorescence Concentration (μg/mL)[a] | Micro-Kjeldahl Concentration (μg/mL) | Percent Difference[b] |
|---|---|---|---|---|---|
| FHA | None | 1 | 1224.8 | 1225.0 | 0.0 |
| | | 2 | 1143.0 | 973.4 | 16.0 |
| PRN | None | 1 | 227.7 | 221.7 | 2.7 |
| | | 2 | 240.8 | 224.2 | 7.1 |
| FHA | 0.66 mg Al/mL $AlPO_4$ | 1 | 1062.7 | 923.0 | 14.1 |
| | | 2 | 882.7 | 807.0 | 9.0 |
| PRN | 0.66 mg Al/mL $AlPO_4$ | 1 | 158.2 | 148.0 | 6.6 |
| | | 2 | 145.3 | 150.0 | 3.2 |

[a]Concentrations were back calculated by using linear regression of the respective intrinsic fluorescence standard curve.

TABLE 5-continued

Testing the accuracy of intrinsic fluorescence against micro-
Kjeldahl for determining protein concentration in adjuvants

| Antigen | Adjuvant | Lot | Intrinsic Fluorescence Concentration (μg/mL)[a] | Micro-Kjeldahl Concentration (μg/mL) | Percent Difference[b] |
|---|---|---|---|---|---|

[b]Percent difference = [(calculated concentration from technique 1 − calculated concentration from technique 2)/(|calculated concentration from technique 1 + calculated concentration from technique 2|)/2] × 100.

2I. In-Line Method: Fluorescence Flow Cell Proof of Concept—Part A

A proof of concept (POC) study was conducted to prove the functionality and accuracy of a prototype system that incorporated a fluorescence probe attached to a disposable flow cell. Such in-line fluorescence measurement was performed by integrating a flow cell in the processing line, thus avoiding the need for off-line sampling. The flow cell was placed in a black box to avoid ambient light interference. The fiber optic cables that consist of the source and return were connected the photometer and the flow cell. A light source with a wavelength of 280 nm was used to excite the electrons in the sample through an optical window. The emitted photon was detected by a back scattering photodetector positioned at the same angle as the source. The emission filter was placed in front of the detector to allow photons with only 337 nm to pass through and to block any undesired wavelength of light.

The intensity of fluorescence is proportional to the amount of fluorophore (aromatic amino acids), and hence it is proportional to the concentration of the protein. Based on this theory, protein concentration can be quantified based on a calibration curve of the protein of interest. FHA was used as model antigen for the POC study. Calibration curves were generated for adjuvanted and non-adjuvanted FHA. Samples of known FHA concentration were tested to determine preliminary accuracy and precision of the method.

Figure 7:
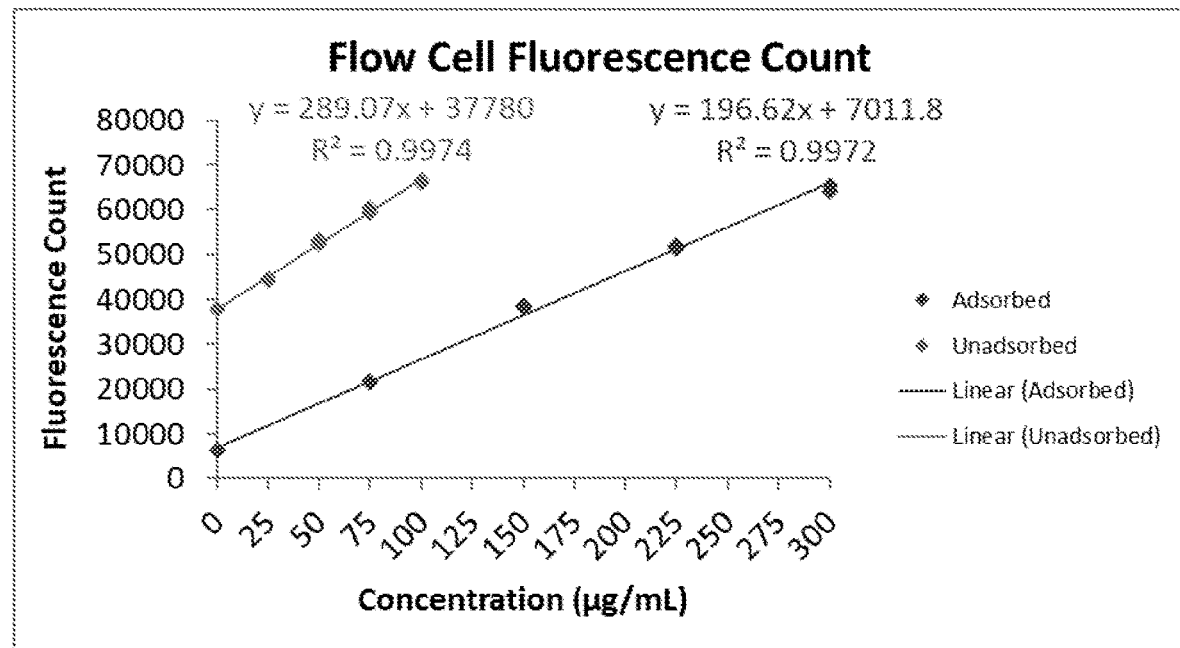
FIG. 7. In-line standard curves for FHA and FHA adsorbed to 0.66 mg Al/mL AlOOH in TBS.

The correlation between FHA concentration and fluorescence signal showed a linear response, $R^2 > 0.99$, for both FHA alone and adsorbed to 0.66 mg Al/mL AlOOH in TBS (FIG. 7).

The in-line method showed high reproducibility for both FHA alone and adsorbed to 0.66 mg Al/mL AlOOH in TBS—coefficient of variation <18.4%, even when using various batches of flow cells (Table 6).

TABLE 6

Comparison of the slopes of multiple replicates
of in-line calibrations curves for FHA alone
and adsorbed to 0.66 mg Al/mL AlOOH in TBS.

| | Slope of Curve | |
|---|---|---|
| Calibration | Unadsorbed[a] | Adsorbed[b] |
| Calibration 1 | 289.1 | 213.9 |
| Calibration 2 | 288.5 | 211.5 |
| Calibration 3 | 392.0 | 211.9 |
| Calibration 4 | — | 240.4 |
| Calibration 5 | — | 194.4 |
| Calibration 6 | — | 185.5 |
| Coefficient of Variation | 18.4% | 9.0% |

[a] The 3 calibration curves for the unadsorbed FHA were done across 2 different lots of flow cells.
[b] The 6 calibration curves for the adsorbed FHA were done across 4 different lots of flow cells.

The in-line method showed high accuracy for both FHA alone and adsorbed to 0.66 mg Al/mL AlOOH in TBS—accuracy >94% (Table 7).

TABLE 7

Comparison of accuracy of the in-line calibrations curves
for FHA alone and adsorbed to 0.66 mg Al/mL AlOOH in TBS.

| Nominal FHA Concentration (μg/mL) | Unadsorbed Measurement (μg/mL) | Accuracy | Adsorbed Measurement (μg/mL) | Accuracy |
|---|---|---|---|---|
| 300 | — | — | 293.91 | 98% |
| 150 | — | — | 157.10 | 95% |
| 100 | 93.33 | 93% | — | — |
| 75 | — | — | 73.69 | 98% |
| 50 | 49.72 | 99% | — | — |
| 25 | 22.55 | 90% | — | — |
| 10 | — | — | 11.13 | 89% |
| Average | — | 94% | — | 95% |

2J. In-Line Method: Fluorescence Flow Cell Proof of Concept—Part B

Additional proof of concept (POC) studies were undertaken to further study the functionality and accuracy of the prototype system incorporating a fluorescence probe attached to a disposable flow cell.

PRN (+/−AlPO$_4$) and A05, a *Neisseria meningitides* serogroup B antigen (+/−AlPO$_4$), were utilized in separate experiments. PRN has 19 tyrosines and 13 trytophans. A05 has 10 phenylalanines and 5 tyrosines. As AlPO$_4$ lacks of any conjugated electrons to fluoresce, proteins that are adsorbed to the adjuvant can also be measured by intrinsic fluorescence, although the light scattering of adjuvant particles and the Al may have influence in the accuracy of the measurement due to its ionic form.

For each protein composition, protein concentration and % adsorption were calculated using the fluorescence flow cell (as in FIG. 8). The excitation and emission wavelength used and collected in this study were 280 nm and 337 nm, respectively. Samples with five evenly spaced concentrations were selected to construct standard curves (Table 8). The accuracy of the standard curves was then verified against another five formulations within the calibration range.

TABLE 8

| Antigen | Calibration Range (μg/mL) | AlPO$_4$ Concentration (mg Al/mL) | Dilution Buffer |
|---|---|---|---|
| PRN | 0-120 | 0.66 | TBS (10 mM in Tris HCl and 150 mM NaCl, pH 7.4) |
| A05 | 0-300 | 0.50 | 10 mM histidine buffered saline, pH 6.0 |

Each of the proteins tested, whether unadjuvanted and or AlPO$_4$-adjuvanted, displayed excellent linear relation ($R^2 > 0.98$) when determining protein concentration. The technique was able to quantify the operating range (Table 8) of adsorbed drug substance for these antigens (data not shown). Unlike the other antigens, A05 lacks tryptophan, the amino acid that contributes the most to the florescence intensity of a protein. Nevertheless, the in-line method was able to produce excellent linear results in the standard curve when A05 was tested. Tyrosine and phenylalanine-based antigens such as A05 are therefore also suitable for intrinsic fluorescence measurement by flow cell, despite inherent weak florescence intensity Percent (%) adsorption of AlPO$_4$ was determined in-line after the adjuvant particles are settled out of the flow cell. This allows the fluorescence probe to only measure the fluorescence of the supernatant. To assist the settling process and avoid clogging, samples were briefly pumped through the tubing for one second after initial 20 min sedimentation, followed by an additional 25 min of settlement for a total duration of 45 min. Percent (%) adsorption was calculated based on the measured supernatant fluorescence converted to concentration and theoretical adsorbed sample concentration. Under these conditions, flow cell was able to produce comparable result for fully adsorbed A05 as well as partially adsorbed A05 corrected by offset and correction factor, in comparison to results by SDS-PAGE. The correction factor and offset may also vary depending on the antigen batch difference, storage condition and filtration status.

IV. Comments

The determination of protein concentration in the presence of aluminum salt adjuvant is an intricate task due to the inherent particulate nature of the adjuvant and the very often strong antigen adsorption to adjuvant particles. To circumvent the turbidity-driven interference, the use of intrinsic fluorescence (IF) for the quantification of proteins in aluminum salt adjuvanted vaccines was explored. Here it is demonstrated that IF from proteins can be detected in the presence of the two more commonly used aluminum salt adjuvants and it can produce linear responses. The results indicate that the IF assay is highly accurate, reproducible and sensitive to quantify protein antigens well within the range of concentrations used in most vaccines.

Many advantages are apparent for the IF method when compared to traditional methods normally used for the determination of protein concentration in vaccines. In contrast to classic methods, the IF assay is extremely simple, non-destructive, and requires minimal assay development. In this context, the IF method was shown to produce comparable results with micro-Kjeldahl, a method that is widely used for the determination of total protein in biopharmaceutical products and vaccines [13,23]. Another advantage of the IF method is that it can be directly applied to the vaccine sample without the need for desorption, dissolution or chemical reactions. The nondestructive and non-invasive nature of IF are maybe the most important features of the assay, which are essential for the implementation of Process Analytical Technology (PAT) tools and to support Quality by Design (QbD) approaches [24,25]. The PAT concept actually arms at understanding the processes by monitoring quality attributes in real time [25]. As such, there is a need for non-destructive methods of quantification that can be applied in/on-line to increase testing efficiency and consistency, while also reducing over-processing and number of rejects. The IF method can be adapted for in-process monitoring of antigen concentration during vaccine manufacturing using in-line fluorimeters [26].

Described herein is a direct, non-destructive, simple and inexpensive fluorimetric assay for the determination of protein concentration in vaccines containing commonly used aluminum salt adjuvants. The method exhibited high accuracy, sensitivity and reproducibility within the protein concentration range found in most vaccines. The application of this technique is not limited to determination of protein concentration in aluminum adjuvant containing vaccines, as it has great potential for the quantification of proteins formulated with other types of adjuvant systems, such as cationic peptide-CpG, squalene emulsions, saponins, liposomes, etc.

While the invention has been described with reference to certain particular embodiments thereof, those skilled in the art will appreciate that various modifications may be made without departing from the spirit and scope of the invention. The scope of the appended claims is not to be limited to the specific embodiments described.

REFERENCES

All patents and publications mentioned in this specification are indicative of the level of skill of those skilled in the art to which the invention pertains. Each cited patent and publication is incorporated herein by reference in its entirety. All of the following references have been cited in this application:

[1] Agnolon V, Bruno C, Galletti B, Mori E, Ugozzoli M, Pergola C, et al. Multiplex immunoassay for in vitro characterization of acellular pertussis antigens in combination vaccines. Vaccine 2016; 34:1040-6.

[2] Katkocin D M, Hsieh C-L. Pharmaceutical Aspects of Combination Vaccines. In: Ellis R W, editor. Comb. Vaccines, Totowa, N. J.: Humana Press; 1999, p. 51-93.

[3] Baldwin S L, Bertholet S, Reese V A, Ching L K, Reed S G, Coler R N. The Importance of Adjuvant Formulation in the Development of a Tuberculosis Vaccine. J Immunol 2012; 188:2189-97.

[4] Carter D, Reed S G. Role of adjuvants in modeling the immune response: Curr Opin HIV AIDS 2010; 5:409-13.

[5] Reed S G, Orr M T, Fox C B. Key roles of adjuvants in modern vaccines. Nat Med 2013; 19:1597-608.

[6] Hutcheon C J, Becker J O, Russell B A, Bariola P A, Peterson G J, Stroop S D. Physiochemical and functional characterization of antigen proteins eluted from aluminum hydroxide adjuvant. Vaccine 2006; 24:7214-25.

[7] Rinella J V, Workman R F, Hermodson M A, White J L, Hem S L. Elutability of Proteins from Aluminum-Containing Vaccine Adjuvants by Treatment with Surfactants. J Colloid Interface Sci 1998; 197:48-56.

[8] Fox C B, Kramer R M, Barnes V L, Dowling Q M, Vedvick T S. Working together: interactions between vaccine antigens and adjuvants. Ther Adv Vaccines 2013; 1:7-20.

[9] Zhu D, Saul A, Huang S, Martin L B, Miller L H, Rausch K M. Use of o-phthalaldehyde assay to determine protein contents of Alhydrogel-based vaccines. Vaccine 2009; 27:6054-9.

[10] Hem S L, HogenEsch H, Middaugh C R, Volkin D B. Preformulation studies—The next advance in aluminum adjuvant-containing vaccines. Vaccine 2010; 28:4868-70.

[11] Ugozzoli M, Laera D, Nuti S, Skibinski D A G, Bufali S, Sammicheli C, et al. Flow cytometry: An alternative method for direct quantification of antigens adsorbed to aluminum hydroxide adjuvant. Anal Biochem 2011; 418: 224-30.

[12] Amari J V, Levesque P, Lian Z, Lowden T, deAlwis U. Concentration determination of a recombinant vaccine antigen adsorbed onto an alum adjuvant by chemiluminescent nitrogen detection. Pharm Res 2005; 22:33-7.

[13] Wang H, Pampati N, McCormick W M, Bhattacharyya L. Protein Nitrogen Determination by Kjeldahl Digestion and Ion Chromatography. J Pharm Sci 2016; 105:1851-7.

[14] Eftink M R. Intrinsic Fluorescence of Proteins. In: Lakowicz J R, editor. Top. Fluoresc. Spectrosc., vol. 6, Boston: Kluwer Academic Publishers; 2002, p. 1-15.

[15] Ghisaidoobe A, Chung S. Intrinsic Tryptophan Fluorescence in the Detection and Analysis of Proteins: A Focus on Förster Resonance Energy Transfer Techniques. Int J Mol Sci 2014; 15:22518-38.

[16] Poveda J A, Prieto M, Encinar J A, Gonzalez-Ros J M, Mateo C R. Intrinsic Tyrosine Fluorescence as a Tool to Study the Interaction of the Shaker B "Ball" Peptide with Anionic Membranes. Biochemistry (Mosc) 2003; 42:7124-32.

[17] ICH Expert Working Group. Validation of Analytical Procedures: Text and Methodology Q2(R1). Step 4 version 2015.

[18] Ma T, Zuazaga G. Micro-Kjeldahl Determination of Nitrogen. A New Indicator and an Improved Rapid Method. Ind Eng Chem Anal Ed 1942; 14:280-2.

[19] Lakowicz J R, Geddes C D, editors. Topics in Fluorescence Spectroscopy. New York: Plenum Press; 1991.

[20] Hem S L, Johnston C T. Production and Characterization of Aluminum-Containing Adjuvants. Vaccine Dev. Manuf., Hoboken, N. J., USA: John Wiley & Sons, Inc.; 2014, p. 319-46.

[21] Denoel P, Poolman J, Carletti G, Veitch K. Effects of adsorption of acellular pertussis antigens onto different aluminum salts on the protective activity in an intranasal murine model of Bordetella pertussis infection. Vaccine 2002; 20:2551-5.

[22] Hem S L, Hogenesch H. Relationship between physical and chemical properties of aluminum-containing adjuvants and immunopotentiation. Expert Rev Vaccines 2007; 6:685-98.

[23] Doshi J., Ravetkar S., Ghole V., Rehani K. Comparative quantitation for the protein content of diphtheria and tetanus toxoids by DC protein assay and Kjeldahl method. Biologicals 2003; 31:187-9.

[24] Pramod K, Tahir Ma, Charoo N, Ansari S, Ali J. Pharmaceutical product development: A quality by design approach. Int J Pharm Investig 2016; 6:129.

[25] Bakeev K A, editor. Process Analytical Technology: Spectroscopic Tools and Implementation Strategies for the Chemical and Pharmaceutical Industries. Chichester, U K: John Wiley & Sons, Ltd; 2010.

[26] Faassen S, Hitzmann B. Fluorescence Spectroscopy and Chemometric Modeling for Bioprocess Monitoring. Sensors 2015; 15:10271-91.

[27] (Guidance for Industry PAT—A Framework for Innovative Pharmaceutical Development, Manufacturing, and Quality Assurance, Pharmaceutical CGMPs, September 2004).

What is claimed is:

1. A method for determining the concentration of a selected compound in a composition comprising an adjuvanted complex of the selected compound, said method comprising:
   (a) obtaining a fluorescence intensity value for a composition comprising an adjuvanted complex of a selected compound, wherein the selected compound includes at least one aromatic amino acid, and wherein said composition is excited at a wavelength of between 250 and 300 nm, and emission spectrum is determined at a wavelength of between 300 and 500 nm to obtain the fluorescence intensity value for the composition; and
   (b) comparing the fluorescence intensity value obtained in (a) with a calibration curve prepared using fluorescence values of at least three calibration samples comprising different known concentrations of a representative compound that is representative of the selected compound to thereby determine the concentration of the selected compound in the composition comprising the adjuvanted complex of the selected compound assayed in (a).

2. The method of claim 1, wherein the calibration curve of (b) is prepared using at least three calibration samples comprising different known concentrations of the representative compound, wherein the representative compound in said calibration samples is excited at a wavelength of between 250 and 300 nm, and wherein emission spectra are determined at a wavelength of between 300 and 500 nm for each of the calibration samples.

3. The method of claim 1, wherein the calibration curve of (b) is prepared using at least five calibration samples comprising different known concentrations of the representative compound.

4. The method of claim 1, wherein the calibration curve of (b) is prepared by:
   (a) preparing at least five calibration samples of the representative compound having concentrations representing about 50%, 75%, 100%, 125% and 150% of the suspected concentration of the selected compound in the composition comprising an adjuvanted complex of the selected compound;
   (b) exciting each calibration sample of (a) using a wavelength of between 250 and 300 nm;
   (c) determining emission spectra of each sample of (b) using a wavelength of between 300 and 500 nm that produces maximum fluorescence intensity for each calibration sample;
   (d) plotting values of fluorescence intensity, at the wavelengths of (c) that produced the maximum fluorescence intensity, against the concentration of the representative compound in the calibration samples, thereby preparing a calibration curve of the representative compound.

5. The method of claim 1, wherein the selected compound is selected from the group consisting of a peptide, polypeptide, protein, polysaccharide-protein conjugate, virus-like particle or viral suspension.

6. The method of claim 1, wherein the representative compound is identical to the selected compound.

7. The method of claim 1, wherein the representative compound has at least 90% sequence identity to the selected compound.

8. The method of claim 1, wherein the representative compound is an adjuvanted complex of the representative compound.

9. The method of claim 1, wherein the excitation wavelength is between 280 and 290 nm, and the emission spectrum is determined at a wavelength of between 320 and 360 nm.

10. The method of claim 1, wherein obtaining a fluorescence intensity value is via a fluorescence probe attached to a flow cell.

11. The method of claim 1, wherein said method is performed in-line, on-line, or off-line.

12. The method of claim 1, wherein the selected compound is adjuvanted with one or more adjuvants selected from the group consisting of an aluminum salt, an emulsion, a peptide, a nucleic acid, and a combination thereof.

13. The method of claim 12, wherein the aluminum salt is one or more of AlOOH, and $AlPO_4$.

14. The method of claim 1, wherein the aromatic amino acid is selected from the group consisting of tryptophan, tyrosine, and phenylalanine.

15. The method of claim 1, wherein intrinsic fluorescence of the selected compound is determined.

16. The method of claim 1, wherein intrinsic fluorescence of the selected compound is determined in the absence of an added fluorescing probe or marker.

17. The method of claim 1, wherein the selected compound has an emission maximum of between about 320 and 360 nm.

\* \* \* \* \*